United States Patent [19]
Hawkins et al.

[11] Patent Number: 5,612,468
[45] Date of Patent: Mar. 18, 1997

[54] PTERIDINE NUCLETIDE ANALOGS AS FLUORESCENT DNA PROBES

[75] Inventors: Mary E. Hawkins, Potomac, Md.; Wolfgang Pfleiderer, Constance, Germany; Michael D. Davis, Rockville; Frank Balis, Bethesda, both of Md.

[73] Assignee: The United States of America as represented by the Department of Health and Human Services, Washington, D.C.

[21] Appl. No.: 451,641

[22] Filed: May 26, 1995

Related U.S. Application Data

[62] Division of Ser. No. 245,923, May 18, 1994.
[51] Int. Cl.$^6$ .................................................. C07H 21/04
[52] U.S. Cl. .................................... 536/22.1; 536/24.3
[58] Field of Search ............................. 536/23.1, 22.1, 536/24.3; 514/248; 544/258; 260/211.5

[56] References Cited

U.S. PATENT DOCUMENTS

| | | | |
|---|---|---|---|
| 3,792,036 | 2/1974 | Pfleiderer | 260/211.5 R |
| 3,798,210 | 3/1974 | Pfleiderer | 260/211.5 R |
| 4,371,514 | 2/1983 | Nagatsu et al. | 424/1 |
| 5,270,465 | 12/1993 | Ferrand et al. | 544/258 |
| 5,278,043 | 1/1994 | Bannwarth et al. | 536/23.1 |
| 5,350,749 | 9/1994 | Hackler et al. | 514/248 |

FOREIGN PATENT DOCUMENTS

0439036A2  12/1991  European Pat. Off. .

OTHER PUBLICATIONS

Bannwrath, W. et al., "Energy Transfer from a Lumazine(= Pteridine–2,4(1H,3H)–dione) Chromophore to Bathophenanthroline–ruthenium (II) Complexes during Hybridization Processes of DNA", Helvetica Chimica Acta, vol. 74, 2000–2007 (1991).
Bannwrath, W. et al., "Energy Transfer within Oligonucleotides from a Lumazine (=Pterine–2, 4(1H, 3H)–dione) Chromophore to Bathophenanthroline–tuthenium(II) Complexes", Helvetica Chimica Acta, vol. 74, 1991–1999 (1991).
Bannwarth, W. et al., "Synthesis and Properties of Dinucleoside Monophosphates with Thymidine and 1–(2'–Deoxy–β–D–ribofuranosyl) lumazines as Building Blocks**)", Liebigs Ann. Chem., 50–65 (1980).
Cao, X. et al., "Structure of Lumazine N$^1$–(2'–Deoxy–D–ribonucleosides) (=1–)2'–Deoxy–D–ribofuranosyl) pteridine–2,4(1H, 3H)–diones): A Revision of the Anomeric Configuration", Helvetica Chimica Acta, vol. 75, 1267–1273 (1992).
Charubala, R. et al., "Synthesis and Properties of Trinucleoside Diphosphates with Thymidine, 2'–Deoxyadenosine, and 1–(2'–Deoxy–αand 1–(2'–Deoxy–β–D–ribofuranosyl) lumazines as Building Blocks**)", Liebigs Ann. Chem., 65–79 (1980).
Davis, M. et al., "Charge Transfer Complexes between Pteridine Substrates and the Active Center Molybdenum of Xanthine Oxidase", J. Biol. Chem., 257, vol. 24, 14730–14737 (1982).
Davis, M. et al., "The Reaction of Xanthine Oxidase with Lumazine", J. Biol. Chem., 259 vol. 6, 3526–3533 (1984).
Harris, R. et al., "Synthesis and Properties of 4–Amino–8–β–D–ribofuranosyl–7 (8H)–pteridinone and its 2–und 6–Phenyl Derivatives", Liebigs Ann. Chem., 1457–1468 (1981).
Himmelsbach, F. et al., "The p–Nitrophenylethyl (NPE) Group: A Versatile New Blocking Group for Phosphate and Aglycone Protection in Nucleosides and Nucleotides", Tetrahydron vol. 40, No.1, 59–72 (1984).
Itoh, T. et al., "Ribosidation of 2–Dimethylamino–4, 7–dioxo–tetrehydropteridine and it 4–Benzyloxy Derivative", Chem. Ber., vol. 109, 3228–3242, (1976).
Kiriasis, L. et al., "Synthesis and Properties of New Pteridine Nucleosides", [in?] Chemistry and Biology of Pteridines, Kisliuk/Brown, eds., 49–53 (1979).
Ott, M. et al., "Synthesis of 4–Amino–7–oxo–7, 8–dihydropteridine–N–8–βD–ribofuranoside A Structural Analogue of Adosine", Chem. Ber. vol. 107, 339–361, (1974).
Ritzmann, G. et al., "Improved Syntheses of Lumazine Nucleosides", Liebigs Ann. Chem., 1217–1234 (1977).
Ritzmann, G. et al., "Synthesis and Properties of Lumazine Nucleotides –Structural Analogs of Urdine and Thymidine", vol. 106, 1407–1417 (1973).
Schmid, H. et al., "Synthesis of Isoxanthopterin–N–8–β–D–ribofuranoside –A Structural Analog of the Nucleoside Guanosine", Chem. Ber. vol. 106, 1952–1975 (1973).
Taira, et al. "Evaluation of the Importance of Hydrophobic Interactions in Drug Binding to Dihydrofolate Reductase", J. Med. Chem. vol. 31, 1129–137 (1988).

*Primary Examiner*—W. Gary Jones
*Assistant Examiner*—Amy Atzel
*Attorney, Agent, or Firm*—Townsend and Townsend and Crew LLP

[57] ABSTRACT

The invention provides novel pteridine nucleotides which are highly fluorescent under physiological conditions and which may be used in the chemical synthesis of fluorescent oligonucleotides. The invention further provides for fluorescent oligonucleotides comprising one or more pteridine nucleotides. In addition the invention provides for pteridine nucleotide triphosphates which may be used as the constituent monomers in DNA amplification procedures.

20 Claims, No Drawings

PTERIDINE NUCLETIDE ANALOGS AS FLUORESCENT DNA PROBES

This is a Division of application Ser. No. 08/245,923 filed May 18, 1995.

BACKGROUND OF THE INVENTION

Synthetic oligonucleotides find numerous uses in molecular biology as probes for screening genomic and complementary DNA libraries, as primers for DNA synthesis, sequencing, and amplification, and in the study of DNA-protein interactions. In addition, oligonucleotide probes have proven useful for assaying in vitro gene expression using techniques of in situ hybridization.

Recent improvements in DNA sequencing methods, fluorescent labels, and detection systems have dramatically increased the use of fluorescently labeled oligonucleotides in all of these applications. Typically oligonucleotides are labeled with a fluorescent marker, either directly through a covalent linkage (e.g., a carbon linker), or indirectly whereby the oligonucleotide is bound to a molecule such as biotin or dioxigenin, which, is subsequently coupled to a fluorescently labeled binding moiety (e.g., streptavidin or a labeled monoclonal antibody).

These fluorescent labeling systems, however, suffer the disadvantage that the fluorescent complexes and their binding moieties are relatively large. The presence of large fluorescent labels and associated linkers may alter the mobility of the oligonucleotide, either through a gel as in sequencing, or through various compartments of a cell.

In addition, the presence of these markers alters the interaction of the oligonucleotide with other molecules either through chemical interactions or through steric hinderance. Thus the presence of these markers makes it difficult to study the interactions of DNA with other molecules such as proteins. The study of protein-DNA interactions is of profound interest as they involve some of the most fundamental mechanisms in biology. They include, for example, the progression of a DNA polymerase or reverse transcriptase along the length of the oligonucleotide, the activation of gene transcription as in the AP1 or steroid hormone pathway, or the insertion of viral DNA into the host genome as mediated by the HIV IN enzyme. For these reasons, it is desirable to obtain a fluorescent moiety analogous in structure to a pyrimidine or purine nucleotide and capable of being incorporated into an oligonucleotide. Such a moiety would preferably render the oligonucleotide molecule fluorescent without significantly altering the size or chemical properties of the oligonucleotide.

Numerous analogs of nucleotides are known. Among them are furanosyl pteridine derivatives. Methods of synthesizing these pteridine derivatives, which are structurally analogous to purine nucleotides, are well known. Indeed, a number of pteridine-derived analogs have been synthesized in the hope of discovering new biologically active compounds. Thus, Pfleiderer (U.S. Pat. No. 3,798,210 and U.S. Pat. No. 3,792,036) disclosed a number of pteridine-glycosides which possessed antibacterial and antiviral properties. Pfleiderer, however, did not investigate the fluorescent properties of these compounds.

Similarly, Schmidt et al., *Chem. Ber.* 106: 1952–1975 (1973) describe the ribosidation of a series of pteridine derivatives to produce structural analogs of the nucleoside guanosine, while Harris et al., *Liebigs. Ann. Chem.* 1457–1468 (1981), describe the synthesis of pteridine derivatives structurally analogous to adenosine. Again, neither reference describes measurements of the fluorescent properties of the nucleosides.

The synthesis of oligonucleotides incorporating lumazine derivatives has been described by Bannwarth et al., *Helvetica Chimica Acta.* 74: 1991–1999 (1991), Bannwarth et al., *Helvetica Chimica Acta.* 74: 2000–2007 (1991) and Bannwarth et al., (European Patent Application No. 0439036A2). Bannwarth et al. utilized the lumazine derivative in conjunction with a bathophenanthroline-ruthenium complex as an energy transfer system in which the lumazine derivative acted as an energy donor and the ruthenium complex acted as an energy receptor. Energy transfer occurred when the two compounds were brought into proximity resulting in fluorescence. The system provided a mechanism for studying the interaction of molecules bearing the two groups. The references, however, did not describe the use of a lumazine derivative alone in an oligonucleotide. In addition, Bannwarth recognized that a major disadvantage of the lumazine derivative was the " . . . relatively low extinction coefficient for the long wavelength absorption of the lumazine chromophore ($\epsilon$=8900 m$^{-1}$ cm$^{-1}$ at 324 nm pH 6.9)." Bannwarth et al., *Helv. Chim. Acta.*, 74: 1991–1999 (1991).

The present invention overcomes the limitations of these prior art compounds by providing a number of pteridine nucleotides which are analogous in structure to purine nucleotides, highly fluorescent under normal physiological conditions, and suitable for use in the chemical synthesis of oligonucleotides.

SUMMARY OF THE INVENTION

The present invention provides for pteridine nucleotides of the form:

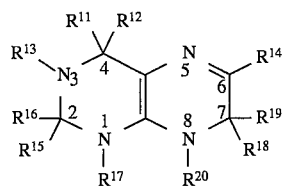

where $R^{11}$ is combined with $R^{12}$ to form a single oxo oxygen joined by a double bond to ring vertex 4, or with $R^{13}$ to form a double bond between ring vertices 3 and 4; $R^{12}$, when not combined with $R^{11}$, is either $NH_2$ or $NH_2$ either mono- or disubstituted with a protecting group; $R^{13}$ when not combined with $R^{11}$ is a lower alkyl or H; $R^{14}$ is either H, lower alkyl or phenyl; $R^{15}$ is combined with $R^{16}$ to form a single oxo oxygen joined by a double bond to ring vertex 2, or with $R^{17}$ to form a double bond between ring vertices 1 and 2, such that ring vertices 2 and 4 collectively bear at most one oxo oxygen; and $R^{16}$ when not combined with $R^{15}$ is a member selected from the group consisting of H, phenyl, $NH_2$, and $NH_2$ mono- or disubstituted with a protecting group. When $R^{15}$ is not combined with $R^{16}$, $R^{18}$ is combined with $R^{19}$ to form a single oxo oxygen joined by a double bond to ring vertex 7. When $R^{15}$ is combined with $R^{16}$, $R^{18}$ is combined with $R^{20}$ to form a double bond between ring vertices 7 and 8, and $R^{19}$ is either H or a lower alkyl. $R^{17}$ when not combined with $R^{15}$, and $R^{20}$ when not combined with $R^{18}$, are compounds of formula:

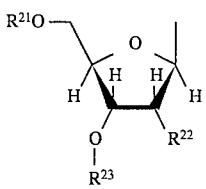

where the symbol $R^{21}$ represents a hydrogen, protecting groups, or a triphosphate; the symbol $R^{22}$ represents a hydrogen, a hydroxyl, or a hydroxyl substituted with a protecting group; and $R^{23}$ represents H, a phosphoramidite, an H-phosphonate, a methyl phosphonate, a phosphorothioate, a phosphotriester, a hemisuccinate, a hemisuccinate covalently bound to a solid support, a dicyclohexylcarbodiimide, and a dicyclohexylcarbodiimide covalently bound to a solid support. When $R^{13}$ is H and $R^{23}$ is H, $R^{21}$ is a triphosphate and when $R^{11}$ is combined with $R^{13}$ to form a double bond between ring vertices 3 and 4 and $R^{23}$ is H, $R^{21}$ is a triphosphate.

These compounds are highly fluorescent under normal physiological conditions, and suitable for use in the chemical synthesis of oligonucleotides. The invention further provides for oligonucleotides that incorporate these pteridine nucleotides.

In addition, the invention provides for pteridine nucleotide triphosphates that may be utilized in various DNA amplification processes. When used in a DNA amplification process, the nucleotide triphosphates are directly incorporated into the amplified DNA sequence rendering it fluorescent. This provides for a rapid assay for the presence or absence of the amplified product.

DESCRIPTION OF THE SPECIFIC EMBODIMENTS

As used herein, the term "lower alkyl" refers to a saturated hydrocarbon radical which may be straight-chain or branched-chain (for example, ethyl, isopropyl, t-amyl, or 2,5-dimethylhexyl). Preferred alkyl groups are those containing one to six carbon atoms. All numerical ranges in this specification and claims are intended to be inclusive of their upper and lower limits.

The term "oligonucleotide" refers to a molecule comprised of two or more deoxyribonucleotides, ribonucleotides, modified ribonucleotides, modified deoxyribonucleotides, ribonucleotide analogs, deoxyribonucleotide analogs, or pteridine derivatives of the present invention. The exact size of an oligonucleotide depends on many factors and the ultimate function or use of the oligonucleotide. Generally, chemically synthesized oligonucleotides range in length from 2 to 200 bases, although, it is well known that oligonucleotides may be ligated together to provide longer sequences. As used herein, the term "oligonucleotide" also encompasses these longer sequences. It is also recognized that double-stranded polynucleotides may be created by hybridization with a complementary sequence or enzymatically through primer extension. The term oligonucleotide as used in this application encompasses both single and double-stranded oligonucleotides.

The term "solid support" refers to a solid material which is functionalized to permit the coupling of a monomer used in polynucleotide synthesis. The solid support is typically coupled to a nucleoside monomer through a covalent linkage to the 3'-carbon on the furanose. Solid support materials typically are unreactive during the polynucleotide synthesis and simply provide a substratum to anchor the growing polynucleotide. Solid support materials include, but are not limited to, polacryloylmorpholide, silica, controlled pore glass (CPG), polystyrene, polystyrene/latex, and carboxyl modified teflon.

The term "cleavage" in reference to solid phase oligonucleotide synthesis refers to the breaking of the bond which binds an oligonucleotide to a solid support. Typically, cleavage involves hydrolysis of a succinate ester bond between the 3'-hydroxyl of an attached oligonucleotide and the solid support.

The term "deprotection" refers to the removal of protecting groups from the exocyclic amines of the heterocyclic bases of an oligonucleotide. Typically, deprotection consists of hydrolysis of an amide moiety consisting of an exocyclic amine and an amino protection group, e.g. benzoyl, p-nitrophenoxycarbonyl, di-n-butylaminomethylidene, and dimethylaminomethylenamino. The term deprotection is also used to refer to the removal of protecting groups from the phosphate diesters (internucleotide phosphates) of the oligonucleotide. When such protecting groups are methoxy, "deprotection" as used herein may not encompass their removal. Instead, additional treatment with a standard thiophenol-containing reagent may be desired to produce a "thiolated" oligonucleotide.

The term "pteridine nucleotide" or "pteridine monomer" is used herein to refer to the furanosyl pteridine derivatives of the present invention with a 3'-phosphate group. It is recognized that properly speaking the furanosyl pteridine derivatives are not nucleotides as the pteridine is neither a purine or a pyrimidine. However, because the furanosyl pteridine derivatives are structurally analogous to purine nucleotides, and the furanosyl pteridines of this invention are used in the same manner as nucleotides both will be referred to as nucleotides. As used herein, the pteridine nucleotide or pteridine monomer may be fully protected for use in polynucleotide synthesis or it may be deprotected when used as a triphosphate or when incorporated into an oligonucleotide.

The term "nucleotide monomer" as used herein refers to pteridine nucleotides, the "standard" nucleotides; adenosine, guanosine, cytidine, thymidine, and uracil, or derivatives of these nucleotides. Such derivatives include, but are not limited to, inosine, 5-bromodeoxycytidine, 5-bromo-deoxyuridine, $N^6$-methyl-deoxyadenosine and 5-methyl-deoxycytidine.

As used herein, the term "protecting group" refers to a group which is joined to or substituted for a reactive group (e.g. a hydroxyl or an amine) on a molecule. The protecting group is chosen to prevent reaction of the particular radical during one or more steps of a chemical reaction. Generally the particular protecting group is chosen so as to permit removal at a later time to restore the reactive group without altering other reactive groups present in the molecule. The choice of a protecting group is a function of the particular radical to be protected and the compounds to which it will be exposed. The selection of protecting groups is well known to those of skill in the art. See, for example Greene et al., *Protective Groups in Organic Synthesis, 2nd ed.*, John Wiley & Sons, Inc. Somerset, N.J. (1991), which is herein incorporated by reference.

As used herein, the term "protected amine" refers to an amine which has been reacted with an amino protecting group. An amino protecting group prevents reaction of the amide function during either the synthesis of the derivatized pteridine nucleoside or during the chemical synthesis of DNA or RNA using that nucleotide. The amino protecting group can be removed at a later time to restore the amino group without altering other reactive groups present in the molecule. For example, the exocyclic amine may be reacted with dimethylformamid-diethylacetal to form the dimethylaminomethylenamino function. Amino protecting groups generally include carbamates, benzyl radicals, imidates, and others known to those of skill in the art. Preferred amino protecting groups include, but are not limited to, p-nitrophenylethoxycarbonyl or dimethyaminomethylenamino.

The term "coupling" is generally used in DNA synthesis to refer to the joining of one nucleotide monomer to another nucleotide monomer or to the 5' terminal of an oligonucleotide. The coupling is generally accomplished by the formation of a phosphodiester linkage from the 3'- phosphate of one nucleotide monomer to the 5'-hydroxyl of a second monomer or oligonucleotide. Coupling is also used to refer to the joining of an initial nucleoside to a solid support.

The term "capping" refers to a step in which unreacted 5'-hydroxyl groups that fail to condense and successfully couple with the next derivatized nucleotide are blocked. This insures that subsequent reactions proceed only by propagating chains of the desired sequence. Typically capping involves the acetylation of the 5'-hydroxyl functions. Usually this is accomplished by acetic anhydride catalyzed by 4-dimethylaminopyridine (DMAP). Other reagents, known to those of skill in the art are suitable.

The term "synthesis cycle" refers to the sequence of reactions necessary to couple a nucleotide monomer to the 5' terminal of the oligonucleotide being synthesized. Typically, a synthesis cycle involves removal of the 5'-hydroxyl blocking group on the terminus of the oligonucleotide, reaction with the phosphite derivative of a nucleotide monomer to form a phosphodiester bond, and then capping of molecules in which coupling was unsuccessful.

The term "normal physiological conditions" is used herein to refer to conditions that are typical inside a living organism or a cell. While it is recognized that some organs provide extreme conditions, the intra-organismal and intracellular environment normally varies around pH 7 (i.e. from pH 6.5 to pH 7.5), contains water as the predominant solvent, and exists at a temperature above 0° C. and below 50° C.

This invention provides a number of pteridine nucleotides which are highly fluorescent under normal physiological conditions and which may be utilized in the chemical synthesis of oligonucleotides to produce fluorescent oligonucleotides. These fluorescent oligonucleotides have many uses including, for example, probes for screening genomic and complementary DNA libraries, probes for in situ hybridization, primers for DNA synthesis, sequencing, and amplification, and as model substrates to investigate DNA-protein interactions.

In one embodiment, the pteridine nucleotides of this invention are suitable for use in the chemical synthesis of oligonucleotides. In general, this requires blocking the exocyclic amines on the pteridine, derivatizing the phosphite moiety with a reactive group appropriate to the particular synthetic chemistry contemplated, and blocking the 5' hydroxyl with a protecting group that may be removed during synthesis to facilitate the stepwise coupling of derivatized nucleotides to the 5' terminus of the growing oligonucleotide. Where the sugar of the pteridine derivative is a ribose, the reactive 2'-hydroxyl group must also be protected.

In a preferred embodiment, the invention provides for nucleotide monomers of formula I.

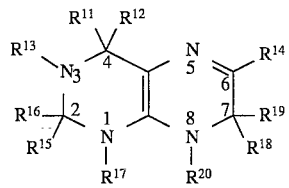

These nucleotide monomers are pteridine derivatives with ting vertices 1 through 8 as shown, where $R^{11}$ is combined with $R^{12}$ to form a single oxo oxygen joined by a double bond to ring vertex 4, or with $R^{13}$ to form a double bond between ring vertices 3 and 4; $R^{12}$, when not combined with $R^{11}$, is either $NH_2$ or $NH_2$ either mono- or disubstituted with a protecting group; $R^{13}$ when not combined with $R^{11}$ is a lower alkyl or H; $R^{14}$ is either H, lower alkyl or phenyl; $R^{15}$ is combined with $R^{16}$ to form a single oxo oxygen joined by a double bond to ring vertex 2, or with $R^{17}$ to form a double bond between ring vertices 1 and 2, such that ring vertices 2 and 4 collectively bear at most one oxo oxygen; and $R^{16}$ when not combined with $R^{15}$ is a member selected from the group consisting of H, phenyl, NH:, and NH: mono- or disubstituted with a protecting group. When $R^{15}$ is not combined with $R^{16}$, $R^{18}$ is combined with $R^{19}$ to form a single oxo oxygen joined by a double bond to ring vertex 7. When $R^{15}$ is combined with $R^{16}$, $R^{18}$ is combined with $R^{20}$ to form a double bond between ring vertices 7 and 8, and $R^{19}$ is either H or a lower alkyl. $R^{17}$ when not combined with $R^{15}$, and $R^{20}$ when not combined with $R^{18}$, are compounds of formula II.

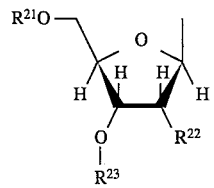

where the symbol $R^{21}$ represents a hydrogen, protecting groups or a triphosphate; the symbol $R^{22}$ represents a hydrogen, a hydroxyl, or a hydroxyl substituted with a protecting group; and $R^{23}$ represents a hydrogen, a phosphoramidite, an H-phosphonate, a methyl phosphonate, a phosphorothioate, a phosphotriester, a hemisuccinate, a hemisuccinate covalently bound to a solid support, a dicyclohexylcarbodiimide, and a dicyclohexylcarbodiimide covalently bound to a solid support. When $R^{13}$ is H and $R^{23}$ is H, $R^{21}$ is a triphosphate and when $R^{11}$ is combined with $R^{13}$ to form a double bond between ring vertices 3 and 4 and $R^{23}$ is H, $R^{21}$ is a triphosphate.

In another preferred embodiment $R^{14}$ is hydrogen, a methyl or a phenyl, more particularly a hydrogen or a methyl.

In still another preferred embodiment, $R^{16}$, when not combined with $R^{15}$, is a hydrogen, a phenyl, an amino group, or $NH_2$ disubstituted with a protecting group. More particularly, $R^{16}$ is a hydrogen and a phenyl.

In yet another preferred embodiment when $R^{18}$ is combined with $R^{20}$, $R^{19}$ is a hydrogen or a methyl.

In still yet another preferred embodiment, $R^{14}$ is a hydrogen, a methyl, or a phenyl, $R^{16}$, when not combined with $R^{15}$, is a hydrogen, a phenyl or an amino, and, when $R^{18}$ is combined with $R^{20}$, $R^{19}$ is a hydrogen or a methyl.

Among the compounds of the present invention, nine embodiments are particularly preferred. In a first preferred embodiment $R^{11}$ is combined with $R^{13}$ to form a double bond between ring vertices 3 and 4; $R^{12}$ is $NH_2$ or $NH_2$ mono- or disubstituted with a protecting group; $R^{14}$ is a hydrogen; $R^{15}$ is combined with $R^{17}$ to form a double bond between ring vertices 1 and 2; $R^{16}$ is a phenyl; $R^{18}$ is combined with $R^{19}$ to form a single oxo oxygen joined by a double bond to ring vertex 7; and $R^{20}$ is formula II. This embodiment is illustrated by formula III. Particularly preferred compounds of this embodiment are illustrated by formula III when $R^{12}$ is $NH_2$.

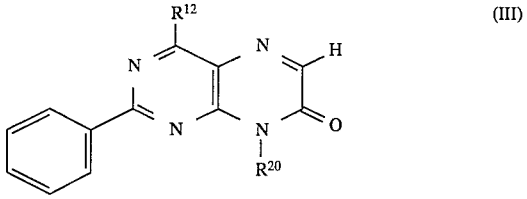
(III)

In a second preferred embodiment $R^{11}$ is combined with $R^{13}$ to form a double bond between ring vertices 3 and 4; $R^{12}$ is $NH_2$ or $NH_2$ mono- or disubstituted with a protecting group; $R^{14}$ is a phenyl; $R^{15}$ is combined with $R^{17}$ to form a double bond between ring vertices 1 and 2; $R^{16}$ is a hydrogen; $R^{18}$ is combined with $R^{19}$ to form a single oxo oxygen joined by a double bond to ring vertex 7 and $R^{20}$ is formula II. This embodiment is illustrated by formula IV. Particularly preferred compounds of this embodiment are illustrated by formula IV when $R^{12}$ is $NH_2$.

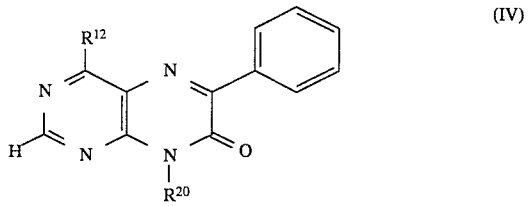
(IV)

In a third preferred embodiment $R^{11}$ is combined with $R^{12}$ to form a single oxo oxygen joined by a double bond to ring vertex 4; $R^{13}$ is $CH_3$; $R^{14}$ is H; $R^{15}$ is combined with $R^{17}$ to form a double bond between ring vertices 1 and 2; $R^{16}$ is $NH_2$; $R^{18}$ is combined with $R^{19}$ to form a single oxo oxygen joined by a double bond to ring vertex 7; and $R^{20}$ is formula II. This embodiment is illustrated by formula V. One particularly preferred compound of this embodiment is the nucleoside illustrated by formula V when $R^{23}$ of formula II is H and more particularly when $R^{21}$, $R^{22}$, and $R^{23}$ of formula II are all H.

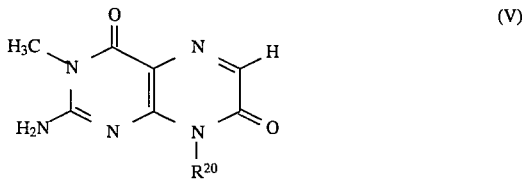
(V)

In a fourth preferred embodiment $R^{11}$ is combined with $R^{12}$ to form a single oxo oxygen joined by a double bond to ring vertex 4; $R^{13}$ is a hydrogen; $R^{14}$ is hydrogen; $R^{15}$ is combined with $R^{17}$ to form a double bond between ring vertices 1 and 2; $R^{16}$ is $NH_2$ or $NH_2$ mono- or disubstituted with a protecting group; $R^{18}$ is combined with $R^{19}$ to form a single oxo oxygen joined by a double bond to ring vertex 7; and $R^{20}$ is formula II. This embodiment is illustrated by formula VI. Particularly preferred compounds of this embodiment are illustrated by formula VI when $R^{16}$ is $NH_2$.

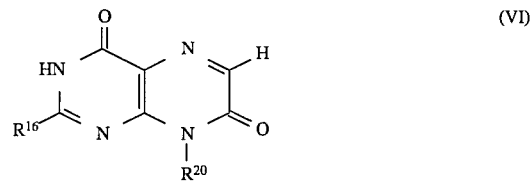
(VI)

In a fifth preferred embodiment $R^{11}$ is combined with $R^{12}$ to form a single oxo oxygen joined by a double bond to ring vertex 4; $R^{13}$ is a hydrogen; $R^{14}$ is $CH_3$; $R^{15}$ is combined with $R^{17}$ to form a double bond between ring vertices 1 and 2; $R^{16}$ is $NH_2$ or $NH_2$ mono- or disubstituted with a protecting group; $R^{18}$ is combined with $R^{19}$ to form a single oxo oxygen joined by a double bond to ring vertex 7; and $R^{20}$ is formula II. This embodiment is illustrated by formula VII. Particularly preferred compounds of this embodiment are illustrated by formula VII when $R^{16}$ is $NH_2$.

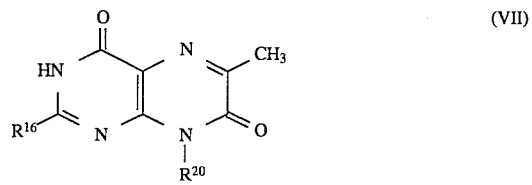
(VII)

In a sixth preferred embodiment $R^{11}$ is combined with $R^{13}$ to form a double bond between ring vertices 3 and 4; $R^{12}$ is $NH_2$ or $NH_2$ mono- or disubstituted with a protecting group; $R^{14}$ is $CH_3$; $R^{15}$ is combined with $R^{16}$ to form a single oxo oxygen joined by a double bond to ring vertex 2; $R^{17}$ is formula II; $R^{18}$ is combined with $R^{20}$ to form a double bond between ring vertices 7 and 8; and $R^{19}$ is $CH_3$. This embodiment is illustrated by formula VIII. Particularly preferred compounds of this embodiment are illustrated by formula VII when $R^{12}$ is $NH_2$.

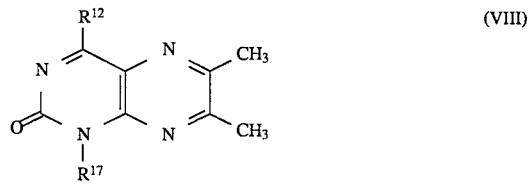
(VIII)

In a seventh preferred embodiment $R^{11}$ is combined with $R^{13}$ to form a double bond between ring vertices 3 and 4; $R^{12}$ is $NH_2$ or $NH_2$ mono- or disubstituted with a protecting group; $R^{14}$ is H; $R^{15}$ is combined with $R^{16}$ to form a single oxo oxygen joined by a double bond to ring vertex 2; $R^{17}$ is formula II; $R^{18}$ is combined with $R^{20}$ to form a double bond between ring vertices 7 and 8; and $R^{19}$ is $CH_3$. This embodiment is illustrated by formula IX. Particularly preferred compounds of this embodiment are illustrated by formula IX when $R^{12}$ is $NH_2$.

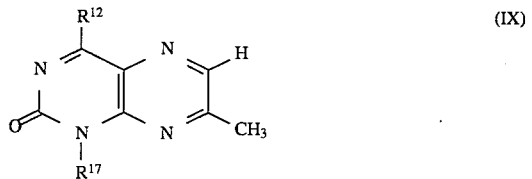
(IX)

In an eighth preferred embodiment $R^{11}$ is combined with $R^{13}$ to form a double bond between ring vertices 3 and 4; $R^{12}$ is $NH_2$; $R^{14}$ is $CH_3$; $R^{15}$ is combined with $R^{16}$ to form a single oxo oxygen joined by a double bond to ring vertex 2; $R^{17}$ is formula II; $R^{18}$ is combined with $R^{20}$ to form a double bond between ring vertices 7 and 8; and $R^{19}$ is H. This embodiment is illustrated by formula X. Particularly preferred compounds of this embodiment are illustrated by formula X when $R^{12}$ is $NH_2$.

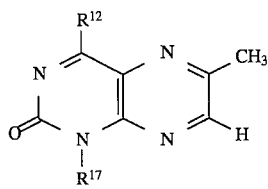
(X)

In a ninth preferred embodiment $R^{11}$ is combined with $R^{13}$ to form a double bond between ring vertices 3 and 4; $R^{12}$ is $NH_2$ or $NH_2$ mono- or disubstituted with a protecting group; $R^{14}$ is H; $R^{15}$ is combined with $R^{16}$ to form a single oxo oxygen joined by a double bond to ring vertex 2; $R^{17}$ is formula II; $R^{18}$ is combined with $R^{20}$ to form a double bond between ring vertices 7 and 8; and $R^{19}$ is H. This embodiment is illustrated by formula III. Particularly preferred compounds of this embodiment are illustrated by formula XI when $R^{12}$ is $NH_2$.

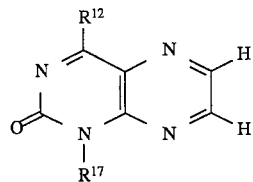
(XI)

As explained above, the exocyclic amines of the pteridines must generally be protected during oligonucleotide synthesis. Protecting groups suitable for blocking the exocyclic amines of the pteridines are widely known to those of skill in the art. In general, a protecting group will prevent undesired reactions of the exocyclic amines during the synthesis of an oligonucleotide incorporating the pteridine derivative. It is of course recognized that these groups may also need to be protected during the actual synthesis of the pteridine derivative to prevent undesired reactions. The protecting group should be removable after synthesis of the oligonucleotide to restore the amine group without altering other reactive groups present in the molecule.

Typically, the amine groups are protected by acylation, usually by carbamates, benzyl radicals, imidates, and others known to those of skill in the art. Examples of protecting groups include, but are not limited to, benzoyl, 4-methoxybenzoyl, phenoxyacetyl, diphenylacetyl, isobutyryl, phthaloyl, di-n-butylaminomethylidene, dimethylaminomethylenamino, dimethylaminomethylidene, p-nitrophenylethoxycarbonyl and dimethylformamide-diethylacetal. Particularly preferred are p-nitrophenylethoxycarbonyl or dimethylaminomethylenamino. For a description of a number of suitable protecting groups see Reese, *Tetrahedron*, 34: 3143–3179 (1978); Ohtsuka et al., *Nucleic Acids Res.*, 10: 6553–6570 (1982), and Narang, *Tetrahedron* 39: 3–22 (1983) which are incorporated herein by reference.

Thus, in a preferred embodiment, the invention provides for nucleotide monomers of formula I in which $R^{12}$ and $R^{16}$ are independently $NH_2$ either mono- or disubstituted by a protecting group selected from the group consisting of benzoyl, isobutyryl, phthaloyl, di-n-butylaminomethylidene, dimethylaminomethylidene, p-nitrophenylethoxycarbonyl and dimethylaminomethylenamino. More particularly, $R^{12}$ is $NH_2$ monosubstituted by a protecting group selected from the group consisting of di-n-butylaminomethylidene, p-nitrophenylethoxycarbonyl, and dimethylaminomethylenamino.

During oligonucleotide synthesis, the 5'-hydroxyl group of the pteridine monomer must be blocked to prevent undesired reactions. However this blocking group must also be removable during synthesis to permit the stepwise coupling of new monomers to the 5' terminus of the growing oligonucleotide. Appropriate protecting groups are well known to those of skill in the art and include, but are not limited to, trityl, monomethoxytrityl, dimethoxytrityl, phthaloyl, di-n-butylaminomethylene, and dimethylaminomethylidene. Dimethoxytrityl is generally preferred as a blocking group for the 5'-hydroxyl group.

Thus, in a preferred embodiment, the invention provides for nucleotide monomers of formula I in which $R^{20}$ is formula II wherein $R^{21}$ is H, trityl, monomethoxytrityl, dimethoxytrityl, phthaloyl, di-n-butylaminomethylene, or dimethylaminomethylidene. More specifically, $R^{21}$ is either dimethoxytrityl, di-n-butylaminomethylene, or dimethylaminomethylidene.

Where the sugar of the pteridine derivative is a ribofuranose, the 2'-hydroxyl group must also be protected. Preferred 2'-hydroxyl protecting groups include, but are not limited to, trityl, monomethoxytrityl, dimethoxytrityl, tetrahydropyran-1-yl, 4-methoxytetrahydropyran-4-yl, 1-(2-chloro-4-methyl)phenyl-4-methoxypiperidin-4-yl, t-butyldimethylsilyl, p-nitrophenylerhysulfonyl, tetrahydropyranyl, 4-methoxytetrahydropyranyl, 2-nitrobenzyl, 9-phenylxanthen-9-yl and p-nitrophenylethyl. In a preferred embodiment, the 2'-hydroxyl group will be protected by substitution with a tertbutyldimethylsilyl group.

Thus in another preferred embodiment, the invention provides for nucleotide monomers of formula I, in which $R^{20}$ is formula II wherein $R^{22}$ is either H, OH, or OH substituted with either trityl, monomethoxytrityl, dimethoxytrityl, tetrahydropyran-1-yl, 4-methoxytetrahydropyran-4-yl, 1-(2-chloro-4-methyl)phenyl-4-methoxypiperidin-4-yl, t-butyldimethylsilyl, p-nitrophenylethylsulfonyl, tetrahydropyranyl, 4-methoxytetrahydropyranyl, 2-nitrobenzyl, 9-phenylxanthen-9-yl and p-nitrophenylethyl. More particularly, $R^{22}$ is either H or OH substituted with either dimethoxytrityl, tetrahydropyran-1-yl, t-butyldimethylsilyl, 2-nitrobenzyl, or p-nitrophenylethyl.

The β-cyanoethyl, N-diisopropyl phosphoramidite compounds of the present invention are preferred as oligonucleotide synthesis monomers. These compounds may generally be utilized in most commercial DNA synthesizers without modification of the synthesis protocol. However, where large scale synthesis is desired, or where it is desirable to incorporate sulfur groups or other modifications in the phosphate linkages, the H-phosphonate compounds of the present invention may be preferred as synthesis reagents. The synthesis and use of other phosphite derivatives suitable for oligonucleotide synthesis is well known to those of skill in the art. These include, but are not limited to a methyl phosphonate, a phosphorothioate, and a phosphotriester.

Preferred embodiments of this invention are the compounds where the pteridine nucleotides are derivatized and protected for use as reagents in the synthesis of oligonucleotides. In particular, the reactive exocyclic amines are protected and the 3'-hydroxyl is derivatized as an H-phosphonate or as a phosphoramidite. Particularly preferred are compounds illustrated by formulas III through XI derivatized in this manner.

Thus, a first preferred embodiment is illustrated by formula III in which $R^{12}$ is $NH_2$ mono- or disubstituted with a protecting group and $R^{20}$ is formula II in which $R^{23}$ is an H-phosphonate or a phosphoramidite. More particularly, $R^{21}$ of formula II is a dimethoxytrityl; $R^{22}$ is H and $R^{23}$ is a β-cyanoethyl, N-diisopropyl phosphoramidite. Still more particularly, $R^{12}$ is dimethylaminomethylenamino.

A second preferred embodiment is illustrated by formula IV in which $R^{12}$ is $NH_2$ mono- or disubstituted with a protecting group and $R^{20}$ is formula II in which $R^{23}$ is an H-phosphonate or a phosphoramidite. More particularly, $R^{21}$ of formula II is a dimethoxytrityl; $R^{22}$ is H and $R^{13}$ is a β-cyanoethyl, N-diisopropyl phosphoramidite. Still more particularly, $R^{12}$ is dimethylaminomethylenamino.

A third preferred embodiment is illustrated by formula V in which $R^{20}$ is formula II and $R^{23}$ is an H-phosphonate or a phosphoramidite. More particularly, $R^{21}$ of formula II is a dimethoxytrityl; $R^{22}$ is H and $R^{23}$ is a β-cyanoethyl, N-diisopropyl phosphoramidite.

A fourth preferred embodiment is illustrated by formula VI in which $R^{16}$ is $NH_2$ mono- or disubstituted with a protecting group and $R^{20}$ is formula II in which $R^{23}$ is an H-phosphonate or a phosphoramidite. More particularly, $R^{21}$ of formula II is a dimethoxytrityl; $R^{22}$ is H and $R^{23}$ is a β-cyanoethyl, N-diisopropyl phosphoramidite. Still more particularly, $R^{16}$ is dimethylaminomethylenamino.

A fifth preferred embodiment is illustrated by formula VII in which $R^{16}$ is $NH_2$ mono- or disubstituted with a protecting group and $R^{20}$ is formula II in which $R^{23}$ is an H-phosphonate or a phosphoramidite. More particularly, $R^{21}$ of formula II is a dimethoxytrityl; $R^{22}$ is H and $R^{23}$ is a β-cyanoethyl, N-diisopropyl phosphoramidite. Still more particularly, $R^{16}$ is dimethylaminomethylenamino.

A sixth preferred embodiment is illustrated by formula VIII in which $R^{12}$ is $NH_2$ mono- or disubstituted with a protecting group and $R^{17}$ is formula II in which $R^{23}$ is an H-phosphonate or a phosphoramidite. More particularly, $R^{21}$ of formula II is a dimethoxytrityl; $R^{22}$ is H and $R^{23}$ is a β-cyanoethyl, N-diisopropyl phosphoramidite. Still more particularly, $R^{12}$ is p-nitrophenylethoxycarbonyl.

A seventh preferred embodiment is illustrated by formula IX in which $R^{12}$ is $NH_2$ mono- or disubstituted with a protecting group and $R^{17}$ is formula II in which $R^{23}$ is an H-phosphonate or a phosphoramidite. More particularly, $R^{21}$ of formula II is a dimethoxytrityl; $R^{22}$ is H and $R^{23}$ is a β-cyanoethyl, N-diisopropyl phosphoramidite. Still more particularly, $R^{12}$ is p-nitrophenylethoxycarbonyl.

An eighth preferred embodiment is illustrated by formula X in which $R^{12}$ is $NH_2$ mono- or disubstituted with a protecting group and $R^{17}$ is formula II in which $R^{23}$ is an H-phosphonate or a phosphoramidite. More particularly, $R^{21}$ of formula II is a dimethoxytrityl; $R^{22}$ is H and $R^{23}$ is a β-cyanoethyl, N-diisopropyl phosphoramidite. Still more particularly, $R^{12}$ is p-nitrophenylethoxycarbonyl.

A ninth preferred embodiment is illustrated by formula XI in which $R^{12}$ is $NH_2$ mono- or disubstituted with a protecting group and $R^{17}$ is formula II in which $R^{23}$ is an H-phosphonate or a phosphoramidite. More particularly, $R^{21}$ of formula II is a dimethoxytrityl; $R^{22}$ is H and $R^{23}$ is a β-cyanoethyl, N-diisopropyl phosphoramidite. Still more particularly, $R^{12}$ is p-nitrophenylethoxycarbonyl.

The oligonucleotides of the present invention may be synthesized in solid phase or in solution. Generally, solid phase synthesis is preferred. Detailed descriptions of the procedures for solid phase synthesis of oligonucleotides by phosphite-triester, phosphotriester, and H-phosphonate chemistries are widely available. See, for example, Itakura, U.S. Pat. No. 4,401,796; Caruthers et al., U.S. Pat. Nos. 4,458,066 and 4,500,707; Beaucage et al., *Tetrahedron Lett.*, 22: 1859–1862 (1981); Matteucci et al., *J. Amer. Chem. Soc.*, 103: 3185–3191 (1981); Caruthers et al., *Genetic Engineering*, 4: 1–17 (1982); Jones, chapter 2, Atkinson et al., chapter 3, and Sproat et al., chapter 4, in Gait, ed. *Oligonucleotide Synthesis: A Practical Approach*, IRL Press, Washington D.C. (1984); Froehler et al., *Tetrahedron Lett.*, 27: 469–472 (1986); Froehler et al., *Nucleic Acids Res.*, 14: 5399–5407 (1986); Sinha et al. *Tetrahedron Lett.*, 24: 5843–5846 (1983); and Sinha et al., *Nucl. Acids Res.*, 12: 4539–4557 (1984) which are incorporated herein by reference.

Generally, the timing of delivery and concentration of reagents utilized in a coupling cycle will not differ from the protocols typical for unmodified commercial phosphoramidites used in commercial DNA synthesizers. In these cases, one may merely add the solution containing the pteridine derivatives of this invention to a receptacle on a port provided for an extra phosphoramidite on a commercial synthesizer (e.g., model 380B, Applied Biosystems, Foster City, Calif., U.S.A.). However, where the coupling efficiency of a particular derivatized pteridine compound is substantially lower than the other phosphoramidites, it may be necessary to alter the timing of delivery or the concentration of the reagent in order to optimize the synthesis. Means of optimizing oligonucleotide synthesis protocols to correct for low coupling efficiencies are well known to those of skill in the art. Generally one merely increases the concentration of the reagent or the amount of the reagent delivered to achieve a higher coupling efficiency. Methods of determining coupling efficiency are also well known. For example, where the 5'-hydroxyl protecting group is a dimethoxytrityl (DMT), coupling efficiency may be determined by measuring the DMT cation concentration in the acid step (which removes the DMT group). DMT cation concentration is usually determined by spectrophotometrically monitoring the acid wash. The acid/DMT solution is a bright orange color. Alternatively, since capping prevents further extension of an oligonucleotide where coupling has failed, coupling efficiency may be estimated by comparing the ratio of truncated to full length oligonucleotides utilizing, for example, capillary electrophoresis or HPLC.

Solid phase oligonucleotide synthesis may be performed using a number of solid supports. A suitable support is one which provides a functional group for the attachment of a protected monomer which will become the 3' terminal base in the synthesized oligonucleotide. The support must be inert to the reagents utilized in the particular synthesis chemistry. Suitable supports are well known to those of skill in the art. Solid support materials include, but are not limited to polacryloylmorpholide, silica, controlled pore glass (CPG), polystyrene, polystyrene/latex, and carboxyl modified teflon. Preferred supports are amino-functionalized controlled pore glass and carboxyl-functionalized teflon.

Solid phase oligonucleotide synthesis requires, as a starting point, a fully protected monomer (e.g., a protected nucleoside) coupled to the solid support. This coupling is typically through the 3'-hydroxyl (oxo when coupled) covalently bound to a linker which is, in turn, covalently bound to the solid support. The first synthesis cycle then couples a nucleotide monomer, via its 3'-phosphate, to the 5'-hydroxyl of the bound nucleoside through a condensation reaction that forms a 3'-5' phosphodiester linkage. Subsequent synthesis cycles add nucleotide monomers to the 5'-hydroxyl of the last bound nucleotide. In this manner an oligonucleotide is synthesized in a 3' to 5' direction producing a "growing" oligonucleotide with its 3' terminus attached to the solid support.

Numerous means of linking nucleoside monomers to a solid support are known to those of skill in the art, although monomers covalently linked through a succinate or hemisuccinate to controlled pore glass are generally preferred. Conventional protected nucleosides coupled through a hemisuccinate to controlled pore glass are commercially available from a number of sources (e.g., Glen Research, Sterling, Vermont, U.S.A., Applied Biosystems, Foster City, Calif., U.S.A., Pharmacia LKB, Piscataway, N.J., U.S.A.).

Placement of a pteridine nucleotide at the 3' end of an oligonucleotide requires initiating oligonucleotide synthesis with a fully blocked furanosyl pteridine linked to the solid support. In a preferred embodiment, linkage of the pteridine nucleoside is accomplished by first derivatizing the pteridine nucleotide as a hemisuccinate. The hemisuccinate may then be attached to amino functionalized controlled pore glass in a condensation reaction using mesitylene-2-sulfonyl chloride/1-methyl- 1H-imidazole as a condensing agent. Controlled pore glass functionalized with a number of different reactive groups is commercially available (e.g., Sigma Chemical, St. Louis, Mo., U.S.A.). A similar coupling scheme is described by Atkinson et al., chapter 3 in Gait, ed., *Oligonucleotide Synthesis: A Practical Approach*, IRL Press, Washington, D.C.,(1984). Triisopropylbenzenesulfonyl chloride, imidazolides, triazolides or even the tetrazolides may also be used as condensing agents. Dicyclohexylcarbodiimide (DCC) and structural analogs are also suitable linkers. Other linkers and appropriate condensing groups are well known to those of skill in the art.

In preferred embodiments, this invention therefore provides for pteridine nucleotides in which the 5'-hydroxyl is derivatized as a hemisuccinate which may then be covalently bound to a solid support; more specifically to controlled pore glass. Particularly preferred are compounds illustrated by formulas III through XI derivatized in this manner.

Thus, in a first preferred embodiment, this invention provides for compounds of formula III where $R^{12}$ is $NH_2$ mono- or disubstituted with a protecting group and $R^{20}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass. Still more particularly $R^{12}$ is dimethylaminomethylenamino.

In a second preferred embodiment, this invention provides for compounds of formula IV where $R^{12}$ is $NH_2$ mono- or disubstituted with a protecting group and $R^{20}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass. Still more particularly $R^{12}$ is dimethylaminomethylenamino.

In a third preferred embodiment, this invention provides for compounds of formula V where $R^{20}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass.

In a fourth preferred embodiment, this invention provides for compounds of formula VI where $R^{16}$ is $NH_2$ mono- or disubstituted with a protecting group and $R^{20}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass. Still more particularly $R^{16}$ is dimethylaminomethylenamino.

In a fifth preferred embodiment, this invention provides for compounds of formula VII where $R^{16}$ is $NH_2$ mono- or disubstituted with a protecting group and $R^{20}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass. Still more particularly $R^{16}$ is dimethylaminomethylenamino.

In a sixth preferred embodiment, this invention provides for compounds of formula VIII where $R^{12}$ is $NH_2$ mono- or disubstituted with a protecting group and $R^{17}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass. Still more particularly $R^{12}$ is p-nitrophenylethoxycarbonyl.

In a seventh preferred embodiment, this invention provides for compounds of formula IX where $R^{12}$ is $NH_2$ mono- or disubstituted with a protecting group and $R^{17}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass. Still more particularly $R^{12}$ is p-nitrophenylethoxycarbonyl.

In an eighth preferred embodiment, this invention provides for compounds of formula X where $R^{12}$ is $NH_2$ mono- or disubstituted with a protecting group and $R^{17}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass. Still more particularly $R^{12}$ is p-nitrophenylethoxycarbonyl.

In a ninth preferred embodiment, this invention provides for compounds of formula XI where $R^{12}$ is $NH_2$ mono- or disubstituted with a protecting group and $R^{17}$ is formula II in which $R^{23}$ is a hemisuccinate, or a hemisuccinate covalently bound to a solid support. More particularly, $R^{21}$ of formula II is a dimethoxytrityl; $R^{22}$ is H; and $R^{23}$ is a hemisuccinate covalently bound to controlled pore glass. Still more particularly $R^{12}$ is p-nitrophenylethoxycarbonyl.

In embodiments where the exocyclic amines are protected by the p-nitrophenylethoxycarbonyl group, the deprotection reagents may also cleave the ester function of the succinyl spacer linking the 3' terminal nucleoside to the solid support. In this case, the coupling scheme described by Stengele et al., *Tetrahedron Lett.*, 18: 2549–2552 (1990) which is incorporated herein by reference, is preferred. In this method, solid supports (dihydroxypropyl-CPG, 500 Å and 1400 Å, Fluka, A G, Switzerland, Catalog Nos: 27754, 27764, 2770) are reacted first with N,N'-carbonyldiimiazole and then with 1,6-bismethylaminohexane as an aliphatic secondary amine spacer. This compound is then coupled with the appropriately protected 2'-nucleoside-3'-O-succinates and the free hydroxyl groups of the solid support are subsequently with acetic anhydride and 4-dimethylaminopyridine (DMAP). This linker is completely stable under the deprotection conditions used for p-nitrophenylethoxycarbonyl and p-nitrophenylethyl groups, while cleavage from the matrix can be achieved normally under hydrolytic conditions in concentrated ammonia in less than two hours.

Once the full length oligonucleotide is synthesized, the protecting groups are removed (the oligonucleotide is deprotected), and the oligonucleotide is then cleaved from the solid support prior to use. (Where a teflon solid support is used, the oligonucleotide may be left permanently attached to the support to produce an affinity column.) Cleavage and deprotection may occur simultaneously or sequentially in any order. The two procedures may be interspersed so that some protecting groups are removed from the oligonucleotide before it is cleaved off the solid support and other groups are deprotected from the cleaved oligonucleotide in solution. The sequence of events depends on the particular blocking groups present, the particular linkage to a solid support, and the preferences of the individuals performing the synthesis. Where deprotection precedes cleavage, the protecting groups may be washed away from the oligonucleotide which remains bound on the solid support. Conversely, where deprotection follows cleavage, the removed protecting groups will remain in solution with the oligonucleotide. Often the oligonucleotide will require isolation from these protecting groups prior to use.

In a preferred embodiment, and most commercial DNA synthesis, the protecting group on the 5'-hydroxyl is removed at the last stage of synthesis. The oligonucleotide is then cleaved off the solid support, and the remaining deprotection occurs in solution. Removal of the 5'-hydroxyl protecting group typically just requires treatment with the same reagent utilized throughout the synthesis to remove the terminal 5'-hydroxyl groups prior to coupling the next nucleotide monomer. Where the 5'-hydroxyl protecting group is a dimethoxytrityl group, deprotection may be accomplished by treatment with acetic acid, dichloroacetic acid or trichloroacetic acid.

Typically, both cleavage and deprotection of the exocyclic amines are effected by first exposing the oligonucleotide attached to a solid phase support (via a base-labile bond) to the cleavage reagent for about 1–2 hours, so that the oligonucleotide is released from the solid support, and then heating the cleavage reagent containing the released oligonucleotide for at least 20–60 minutes at about 80°–90° C. so that the protecting groups attached to the exocyclic amines are removed. The deprotection step may alternatively take place at a lower temperature, but must be carried out for a longer period of time (e.g., the heating can be at 55° C. for 5 hours). In general, the preferred cleavage and deprotection reagent is concentrated ammonia.

Where the oligonucleotide is a ribonucleotide and the 2'-hydroxyl group is blocked with a tert-butyldimethylsilyl(TBDMS) moiety, the latter group may be removed using tetrabutylammonium fluoride in tetrahydrofuran at the end of synthesis. See Wu et al., *J. Org. Chem.* 55: 4717–4724 (1990). Phenoxyacetyl protecting groups can be removed with anhydrous ammonia in alcohol (under these conditions the TBDMS groups are stable and the oligonucleotide is not cleaved). The benzoyl protecting group of cytidine is also removed with anhydrous ammonia in alcohol.

Where the exocyclic amines are protected by the p-nitrophenylethoxycarbonyl group and the coupling to the solid support is via a 1,6-bis-methylaminohexane condensed with succinate nucleoside, the amino groups are preferably deprotected by treatment with a 1M DBU (1,8-diaza-bicyclo [5.4.0]-undec-7-ene). Cleavage of the oligonucleotide from the solid support is then accomplished by treatment with concentrated ammonia.

If this latter approach to deprotection is used, it is preferred to synthesize the oligonucleotide using pteridine, adenine, thymidine, guanosine, cytidine, uracil, and modified nucleotide monomers protected with p-nitrophenyethyl and p-nitrophenylethoxycarbonyl groups for amide and amine protection respectively. See Stengele and Pfleiderer, *Tetrahedron Lett.,* 31: 2549–2552 (1990) citing Barone, et al. *Nucleic Acids Res.,* 12: 4051–4061 (1984). The single deprotection protocol will then deprotect all the constituent nucleotides of the oligonucleotide.

Cleaved and fully deprotected oligonucleotides may be used directly (after lyophilization or evaporation to remove the deprotection reagent) in a number of applications, or they may be purified prior to use. Purification of synthetic oligonucleotides is generally desired to isolate the full length oligonucleotide from the protecting groups that were removed in the deprotection step and, more importantly, from the truncated oligonucleotides that were formed when oligonucleotides that failed to couple with the next nucleotide monomer were capped during synthesis.

Oligonucleotide purification techniques are well known to those of skill in the art. Methods include, but are not limited to, thin layer chromatography (TLC) on silica plates, gel electrophoresis, size fractionation (e.g., using a Sephadex column), reverse phase high performance liquid chromatography (HPLC) and anion exchange chromatography (e.g., using the mono-Q column, Pharmacia-LKB, Piscataway, N.J., U.S.A.). For a discussion of oligonucleotide purification see McLaughlin et al., chapter 5, and Wu et al., chapter 6 in Gait, ed., *Oligonucleotide Synthesis: A Practical Approach*, IRL Press, Washington, D.C., (1984).

The oligonucleotides of the present invention contain pteridine nucleotides at one or more positions in the sequence, either internal to the sequence or terminal. An oligonucleotide of the present invention may contain a single pteridine derivative at one or more locations or may contain two or more different pteridine derivatives. The oligonucleotide may consist entirely of pteridine nucleotides or contain naturally occurring and/or modified nucleotides. Modified nucleotides are well known to those of skill in the art and include, but are not limited to, inosine, 5-bromodeoxycytidine, 5-bromo-deoxyuridine, $N^6$-methyl-deoxyadenosine and 5-methyl-deoxycytidine. Phosphoramidite forms of these nucleotides are commercially available from a number of suppliers including, for example, Applied Biosystems, Inc. Foster City, Calif., U.S.A., Clonetech, Palo Alto, Calif., U.S.A., and Glen Research, Sterling, Vermont, U.S.A.

In a preferred embodiment, this invention provides for oligonucleotides comprising one or more nucleotide monomers having formula XII.

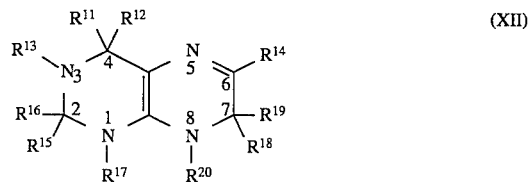

(XII)

The nucleotide monomers are pteridine derivatives with ring vertices 1 through 8 as shown where $R^{11}$ through $R^{16}$, $R^{18}$, and $R^{19}$ are as described for formula I except that the protecting groups are eliminated. Thus, $R^{12}$, when not combined with $R^{11}$, is $NH_2$ and $R^{16}$, when not combined with $R^{15}$, is H, phenyl, or $NH_2$. $R^{17}$, when not combined with $R^{15}$, and $R^{20}$ when not combined with $R^{18}$, are compounds of formula XIII.

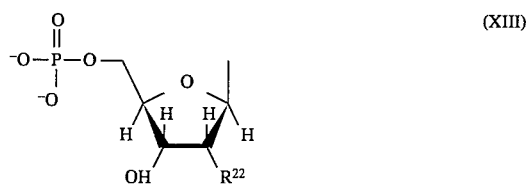

(XIII)

where the symbol $R^{22}$ represents a hydrogen or a hydroxyl.

In a preferred embodiment, the oligonucleotides of the present invention comprise monomers of formula XII where $R^{14}$ is hydrogen, a methyl or a phenyl, more particularly a hydrogen or a methyl.

In another preferred embodiment, the oligonucleotides of the present invention comprise monomers of formula XII where $R^{16}$, when not combined with $R^{15}$, is a hydrogen, a phenyl, or an amino group, more particularly a hydrogen and a phenyl.

In yet another preferred embodiment, the oligonucleotides of the present invention comprise monomers of formula XII where when $R^{18}$ is combined with $R^{20}$, $R^{19}$ is a hydrogen or a methyl.

In a further preferred embodiment, the oligonucleotides of the present invention comprise monomers of formula XII where $R^{14}$ is a hydrogen, a methyl, or a phenyl; $R^{16}$ is a hydrogen, a phenyl or an amino; and, when $R^{18}$ is combined with $R^{20}$, $R^{19}$ is a hydrogen or a methyl.

Among the compounds of the present invention, oligonucleotides comprising one or more of nine nucleotide monomers are particularly preferred. The first preferred nucleotide monomer is illustrated by formula XII where $R^{11}$ is combined with $R^{13}$ to form a double bond between ring vertices 3 and 4; $R^{12}$ is an amino group; $R^{14}$ is a hydrogen; $R^{15}$ is combined with $R^{17}$ to form a double bond between ring vertices 1 and 2; $R^{16}$ is a phenyl, $R^{18}$ is combined with $R^{19}$ to form a single oxo oxygen joined by a double bond to ring vertex 7; and $R^{20}$ is formula XIV. This nucleotide monomer is illustrated by formula XIV where $R^{22}$ is H or OH and more preferably $R^{22}$ is H.

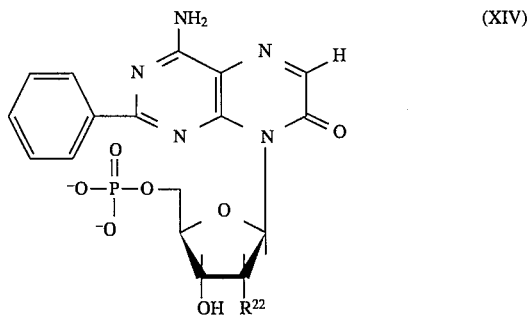

A second preferred nucleotide monomer is illustrated by formula XII where $R^{11}$ is combined with $R^{13}$ to form a double bond between ring vertices 3 and 4; $R^{12}$ is $NH_2$: $R^{14}$ is a phenyl; $R^{15}$ is combined with $R^{17}$ to form a double bond between ring vertices 1 and 2; $R^{16}$ is a hydrogen, $R^{18}$ is combined with $R^{19}$ to form a single oxo oxygen joined by a double bond to ring vertex 7; and $R^{20}$ is formula XIII. This nucleotide monomer is illustrated by formula XV where $R^{22}$ is H or OH and more preferably $R^{22}$ is H.

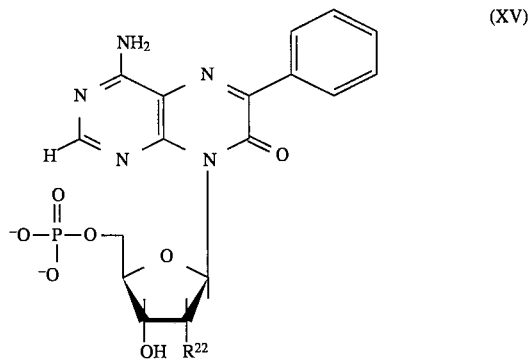

A third preferred nucleotide monomer is illustrated by formula XII where $R^{11}$ is combined with $R^{12}$ to form a single oxo oxygen joined by a double bond to ring vertex 4; $R^{13}$ is $CH_3$; $R^{14}$ is H; $R^{15}$ is combined with $R^{17}$ to form a double bond between ring vertices 1 and 2; $R^{16}$ is $NH_2$; $R^{19}$ is combined with $R^{19}$ to form a single oxo oxygen joined by a double bond to ring vertex 7; and $R^{20}$ is formula XIII. This nucleotide monomer is illustrated by formula XVI where $R^{22}$ is H or OH and more preferably $R^{22}$ is H.

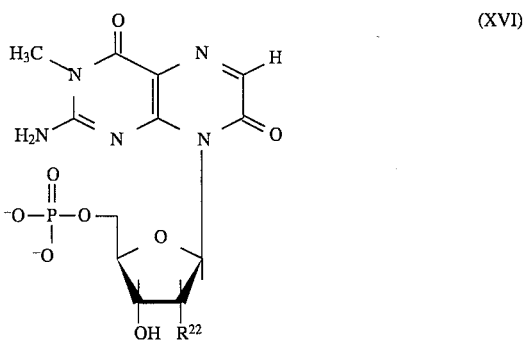

A fourth preferred nucleotide monomer is illustrated by formula XII where $R^{11}$ is combined with $R^{12}$ to form a single oxo oxygen joined by a double bond to ring vertex 4; $R^{13}$ is H; $R^{14}$ is H; $R^{15}$ is combined with $R^{17}$ to form a double bond between ring vertices 1 and 2; $R^{16}$ is $NH_2$; $R^{18}$ is combined with $R^{19}$ to form a single oxo oxygen joined by a double bond to ring vertex 7; and $R^{20}$ is formula XIII. This nucleotide monomer is illustrated by formula XVIII where $R^{22}$ is H or OH and more preferably $R^{22}$ is H.

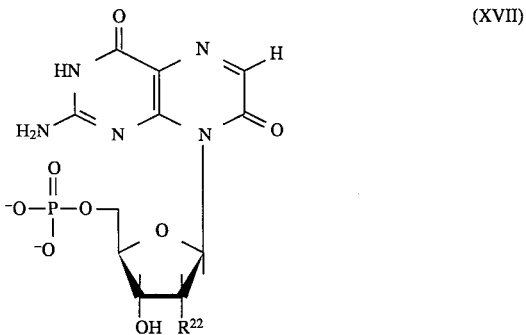

A fifth preferred nucleotide monomer is illustrated by formula XII where $R^{11}$ is combined with $R^{12}$ to form a single oxo oxygen joined by a double bond to ring vertex 4; $R^{13}$ is a hydrogen; $R^{14}$ is $CH_3$; $R^{15}$ is combined with $R^{17}$ to form between ring vertices 1 and 2; $R^{16}$ is $NH_2$; $R^{18}$ is combined with $R^{19}$ to form a single oxo oxygen joined by a double bond to ring vertex 7; and $R^{20}$ is formula XIII. This nucleotide monomer is illustrated by formula XVIII where $R^{22}$ is H or OH and more preferably $R^{22}$ is H.

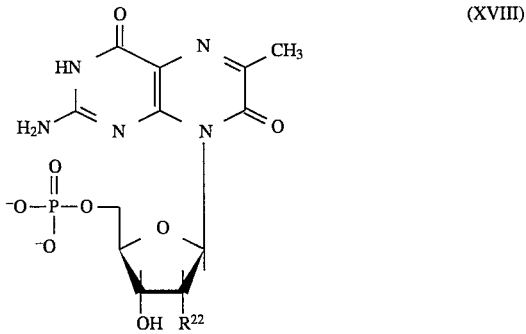

A sixth preferred nucleotide monomer is illustrated by formula XII where $R^{11}$ is combined with $R^{13}$ to form a double bond between ring vertices 3 and 4; $R^{12}$ is $NH_2$; $R^{14}$ is $CH_3$; $R^{15}$ is combined with $R^{16}$ to form a single oxo oxygen joined by a double bond to ring vertex 2; $R^{17}$ is formula XIII; $R^{18}$ is combined with $R^{20}$ to form a double bond between ring vertices 7 and 8; and $R^{19}$ is $CH_3$. This nucleotide monomer is illustrated by formula XIX where $R^{22}$ is H or OH and more preferably $R^{22}$ is H.

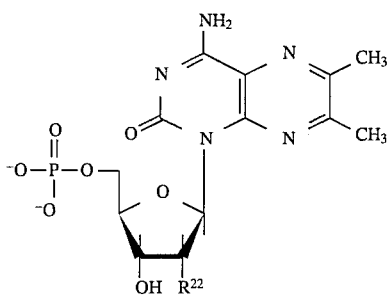

(XIX)

A seventh preferred nucleotide monomer is illustrated by formula XII where $R^{11}$ is combined with $R^{13}$ to form a double bond between ring vertices 3 and 4; $R^{12}$ is $NH_2$; $R^{14}$ is H; $R^{15}$ is combined with $R^{16}$ to form a single oxo oxygen joined by a double bond to ring vertex 2; $R^{17}$ is formula XIII; $R^{18}$ is combined with $R^{20}$ to form a double bond between ring vertices 7 and 8, and $R^{19}$ is $CH_3$. This nucleotide monomer is illustrated by formula XX where $R^{22}$ is H or OH and more preferably $R^{22}$ is H.

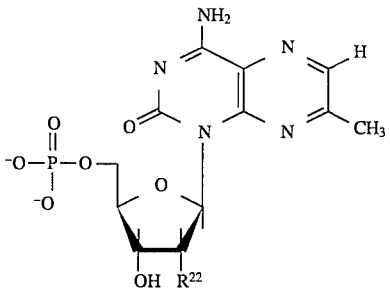

(XX)

An eighth preferred nucleotide monomer is illustrated by formula XII where $R^{11}$ is combined with $R^{13}$ to form a double bond between ring vertices 3 and 4; $R^{12}$ is $NH_2$; $R^{14}$ is $CH_3$; $R^{15}$ is combined with $R^{16}$ to form a single oxo oxygen joined by a double bond to ting vertex 2, $R^{17}$ is formula XIII, $R^{18}$ is combined with $R^{20}$ to form a double bond between ring vertices 7 and 8, and $R^{19}$ is H. This nucleotide monomer is illustrated by formula XXI where $R^{22}$ is H or OH and more preferably $R^{22}$ is H.

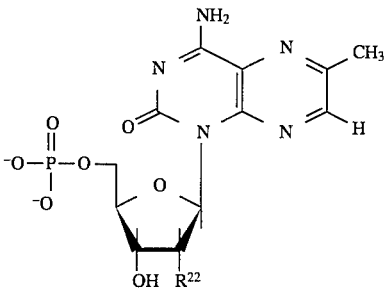

(XXI)

A ninth preferred nucleotide monomer is illustrated by formula XII where $R^{11}$ is combined with $R^{13}$ to form a double bond between ring vertices 3 and 4; $R^{12}$ is $NH_2$; $R^{14}$ is H; $R^{15}$ is combined with $R^{16}$ to form a single oxo oxygen joined by a double bond to ring vertex 2; $R^{17}$ is formula XIII; $R^{18}$ is combined with $R^{20}$ to form a double bond between ring vertices 7 and 8; and $R^{19}$ is H. This nucleotide monomer is illustrated by formula XXII where $R^{22}$ is H or OH and more preferably $R^{22}$ is H.

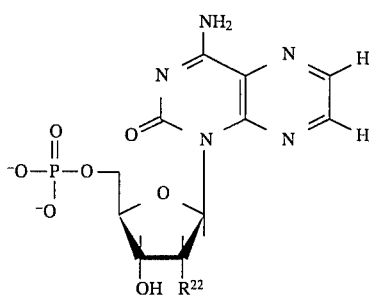

(XXII)

The selection of particular pteridine nucleotides and their position within the oligonucleotide sequence will depend on the particular application for which the oligonucleotide is intended. One of skill in the art would recognize that the fluorescent signal of the pteridine derivative will be affected by pH and the particular chemistry of the neighboring molecules. In general, neighboring purines will tend to quench the signal more than neighboring pyrimidines. Purines as primary neighbors severely quench the signal, and they have a significant effect even as secondary neighbors. Tertiary purines are not as powerful quenchers. In addition, proximity to an end of the nucleotide minimizes the quench of the signal. Thus, where a strong signal is desired from the intact oligonucleotide, it is preferred that the pteridine nucleotides be located at or near a terminus and adjacent to one or more pyrimidines to reduce quenching of the signal. Conversely, where it is desired that the oligonucleotide only provide a signal when it is cut (e.g., by an endonuclease), it is preferred to place the pteridine derivative close to quenching groups (purines), but at a location that is expected to separate the pteridine containing strand from quenching bases when the oligonucleotide is cut thereby releasing the fluorescent signal. The latter approach is illustrated in Example 12.

Thus, in one embodiment, the pteridine nucleotides are located at the 3' end, while in another embodiment, the pteridine nucleotides are located at the 5' end of the oligonucleotides of the present invention.

In yet another embodiment, the oligonucleotides of the present invention comprise pteridine nucleotide monomers which are surrounded by 1 to 10 pyrimidine monomers.

The oligonucleotides of the present invention are not limited to short single stranded sequences. One of skill would recognize that while oligonucleotide synthesis typically has an upper limit of approximately 200 bases, a number of oligonucleotides may be ligated together to form longer sequences. In addition, oligonucleotides having complementary sequences may be hybridized together to form double-stranded molecules. Methods of hybridizing and ligating oligonucleotides to form longer double stranded molecules are well known. See, for example, Sambrook et al., *Molecular Cloning—A Laboratory Manual*, Cold Spring Harbor Laboratory, Cold Spring Harbor, N.Y., 1985).

The pteridine derivatives of the present invention are structurally analogous to naturally occurring purines. When incorporated into an oligonucleotide, they act as a fluorescent tag, but do not alter the physical and chemical properties of the oligonucleotide as severely as currently available fluorescent tags. In some cases the perturbations are so minimal as to allow the oligonucleotide to act as an enzyme substrate permitting the enzyme catalyzed reaction to occur even when the substitution has been made at a site known to be critical for the enzyme function. Thus the oligonucleotides of this invention are particularly useful in the investigation of DNA-protein interactions.

One such interaction is illustrated by the interaction between DNA and the viral integration (IN) protein. Integrase is a viral integration protein that has been implicated in the incorporation of HIV viral genes into the human genome. Engleman et al. *Cell,* 67: 1211–1221 (1991). Thus integrase appears crucial to the HIV infection of cells and may provide an important target for AIDS antiviral research.

A specific DNA sequence (5'-GTG TGG AAA ATC TCT AGC AGT-3') has been used as an effective model for the HIV integrase enzyme. Id. The enzyme functions in a step-wise manner to achieve preparation and actual insertion of the HIV genome into the genome of the host cell. The first step in the mechanism appears to be cleavage of a dinucleotide from the 3' end of the sequence leaving a 5' overhang. Because of their structural similarity to guanosine a number of the pteridine nucleotides of the present invention (e.g., compounds illustrated by formula V or formula VI) may be substituted for the guanosine in the dinucleotide that is cleaved off by integrase. In the intact DNA sequence, the neighboring purine will quench the signal of the pteridine nucleotide. Cleavage of the nucleotide from the strand by integrase releases the quenched fluorescent signal and allows real-time monitoring of the reaction by detecting the increase in fluorescence. This provides a simple and rapid assay for the activity of the integrase enzyme.

Thus, in still another embodiment, the oligonucleotides of the present invention are DNA sequences that model the U5 end of HIV-1 DNA, act as a substrate for integrase and are selected from the group consisting of:

5'-GTψ TGG AAA ATC TCT AGC AGT-3',
5'-GTG TψG AAA ATC TCT AGC AGT-3',
5'-GTG TGψ AAA ATC TCT AGC AGT-3',
5'-GTG TGG AAA ATC TCT AψC AGT-3',
5'-GTG TGG AAA ATC TCT AGC AψT-3',
5'-GTG TψG AAA ATC TCT AψC AGT-3',
5'-ACT GCT AGA ψAT TTT CCA CAC-3',
5'-ACT GCT AψA GAT TTT CCA CAC-3',
5'-ACT ψCT AGA GAT TTT CCA CAC-3' and
5'-ACT GCT ψGA GAT TTT CCA CAC-3';

where A is an adenosine nucleotide, C is a cytosine nucleotide, G is a guanosine nucleotide, T is a thymidine nucleotide, and ψ is a pteridine nucleotide of formula XVI, formula XVII, or formula XVIII in which $R^{22}$ is H or OH and more preferably $R^{22}$ is H.

Of course, the pteridine nucleotides and pteridine oligonucleotides may be utilized to investigate the interaction of DNA with other molecules in a number of contexts. For example, the pteridine nucleotides of formulas XIX, XX, XXI, and XXII may achieve an energy transfer with most of the other claimed compounds. These compounds may be used to monitor the insertion of foreign DNA into a host genome where a DNA strand containing the nucleotide would be brought into proximity to another DNA strand containing one of the other claimed compounds. This would create an energy transfer with the resulting emission of a new discreet signal.

One of skill would recognize that the pteridine derivatives of this invention may also be used simply as fluorescent labels to label almost any biological molecule. The unprotected pteridines alone may be linked by the pteridine 1N or 8N, either directly or through a linker or spacer to a composition it is desired to label. Alternatively, the pteridine nucleosides may be used as fluorescent labels. They may be linked preferably through the 5'-hydroxyl, the 3'-phosphate, or the 2'-hydroxyl (in the case of a ribofuranose) directly, or through a linker, to the composition it is desired to label. Such labeled compositions may include, but are not limited to, biological molecules such as antibodies, ligands, cell surface receptors, and enzymes.

Methods of detecting fluorescently labeled oligonucleotides in vitro or in vivo are well known to those of skill in the art. These means include, but are not limited to, direct visualization, fluorescence microscopy, fluorometers, photographic detection, detection using image intensifiers, photomultipliers, video cameras, and the like. Of course, the selection of a particular method depends on the particular experiment. For example, where the oligonucleotides are used as an assay for enzyme activity or for energy transfer between a pair of molecules, the reactions may be carried out in solution in a fluorometer. Where the oligonucleotides are used as probes for in situ hybridization, detection may be with an image acquisition system (e.g., using a CCD video camera on a fluorescence microscope coupled to an image processing system).

The nucleotide triphosphate compounds of the present invention may be utilized as monomers for DNA synthesis in DNA amplification techniques such as polymerase chain reaction (Innis, et al., *PCR Protocols. A Guide to Methods and Application.* Academic Press, Inc. San Diego, (1990)), ligase chain reaction (LCR) (see Wu et at., *Genomics,* 4: 560 (1989), Landegren, et al., *Science,* 241: 1077 (1988) and Barringer, et al., *Gene,* 89: 117 (1990)), transcription amplification (see Kwoh, et al., *Proc. Natl. Acad. Sci. (U.S.A.),* 86: 1173 (1989))and self-sustained sequence replication (see Guatelli, et al., *Proc. Natl. Acad. Sci. (U.S.A.),* 87: 1874 (1990). Amplification utilizing the pteridine nucleotides of this invention provides a rapid assay for a particular DNA sequence. Where the presence or absence of a particular DNA sequence is diagnostic of a pathological condition (e.g., AIDS), amplification using the pteridine nucleotide triphosphates provides an extremely sensitive and rapid diagnostic tool.

For example, if PCR amplification is used, a pair of PCR primers will be chosen that are complementary to the DNA sequences flanking the DNA sequence of interest. If the proper target sequences are present in the sample, the DNA sequence between the primers will be amplified. This amplified DNA sequence will contain the pteridine nucleotide triphosphates. The amplified sequence may be separated from the remaining monomers in the mixture by simple size fractionation (e.g., by using an NAP column, Pharmacia-LKB, Piscataway, N.J., U.S.A.) or other techniques well known to those of skill in the art. The presence or absence of the amplified sequence may then be immediately detected by measuring the fluorescence of the remaining mixture.

Alternatively, fluorescence polarization (FP) measurements can be used to detect a positive or negative PCR reaction without the necessity of separating the PCR products from the primers and nucleotide monomers. The technique uses pteridine nucleotide monomers or alternatively relatively short primers, about 25 base pairs each, that incorporate pteridine nucleotide monomers. After the PCR procedure is completed, the resulting mixture is analyzed using FP, by passing a beam of polarized light at an excitatory wavelength through the mixture. If the target sequence is not present in the starting mixture, the fluorescent primers will remain in solution as relatively small single-stranded fragments, or the fluorescent nucleotide monomers will remain in solution as relatively small molecules. Both the monomers or the short primer fragments will emit a relatively scattered and non-polarized fluorescent light. By contrast, if the target sequence is present, the pteridine monomers or the fluorescent primers will be incorporated into larger double-stranded segments which will move more slowly in response to the excitatory signal and the fluorescent light emitted by the mixture will be more polarized. See EP No.: 382433 which describes this technique in greater detail.

Thus the invention provides for pteridine nucleotide triphosphates of formula I. Particularly preferred are the triphosphate compounds of formulas III through XI. Thus a first preferred triphosphate is formula III in which $R^{12}$ is $NH_2$ and $R^{20}$ is formula II in which $R^{21}$ is a triphosphate, $R^{22}$ is H, and $R^{23}$ is H.

A second preferred triphosphate is formula IV in which $R^{12}$ is $NH_2$ and $R^{20}$ is formula II in which $R^{21}$ is a triphosphate, $R^{22}$ is H, and $R^{23}$ is H.

A third preferred triphosphate is formula V in which $R^{20}$ is formula II in which $R^{21}$ is a triphosphate, $R^{22}$ is H, and $R^{23}$ is H.

A fourth preferred triphosphate is formula VI in which $R^{16}$ is $NH_2$ and $R^{20}$ is formula II in which $R^{21}$ is a triphosphate, $R^{22}$ is H, and $R^{23}$ is H.

A fifth preferred triphosphate is formula VII in which $R^{16}$ is $NH_2$ and $R^{20}$ is formula II in which $R^{21}$ is a triphosphate, $R^{22}$ is H, and $R^{23}$ is H.

A sixth preferred triphosphate is formula VIII in which $R^{12}$ is $NH_2$ and $R^{17}$ is formula II in which $R^{21}$ is a triphosphate, $R^{22}$ is H, and $R^{23}$ is H.

A seventh preferred triphosphate is formula IX in which $R^{12}$ is $NH_2$ and $R^{17}$ is formula II in which $R^{21}$ is a triphosphate, $R^{22}$ is H, and $R^{23}$ is H.

A eighth preferred triphosphate is formula X in which $R^{12}$ is $NH_2$ and $R^{17}$ is formula II in which $R^{21}$ is a triphosphate, $R^{22}$ is H, and $R^{23}$ is H.

An ninth preferred triphosphate is formula XI in which $R^{12}$ is $NH_2$ and $R^{17}$ is formula II in which $R^{21}$ is a triphosphate, $R^{22}$ is H, and $R^{23}$ is H.

An additional aspect of the invention relates to kits useful in implementing the above-described assay. These kits take a variety of forms and can comprise one or more containers containing the sequence specific amplification primers and one or more pteridine nucleotide triphosphates. Other optional components of the kit include, for example, a polymerase, means used to separate the monomers from the amplified mixture, and the appropriate buffers for PCR or other amplification reactions. In addition to the above components, the kit can also contain instructions for carrying out the described method.

The claimed pteridine nucleotides can be synthesized by standard methods well known to one of skill in the art. In general, the protected pteridine derivative is reacted with a chlorofuranose having its 3'- and 5'-hydroxyls protected as their 4-chlorobenzoyl or paratoluenesulfonyl esters to produce a pteridine nucleoside. See, for example Kiriasis et al., page 49–53 in *Chemistry and Biology of Pteridines*, Kisliuk and Brown, eds. Elsevier North Holland, Inc. N.Y. (1979), Schmid et al., *Chem. Ber.* 106: 1952–1975 (1973), Pfleiderer U.S. Pat. No. 3,798,210, Pfleiderer, U.S. Pat. No. 3,792,036, Harris et al., *Liebigs Ann. Chem.*, 1457–1468 (1981), which illustrate the synthesis of various pteridine nucleosides and are incorporated herein by reference. See also Examples 1 through 4 which describe the synthesis of pteridine nucleosides. Following coupling, the protecting groups can be removed and the 5'-hydroxyl convened to its dimethoxytrityl ether. Subsequent conversion of the 3'-hydroxyl to the H-phosphonate, phosphoramidite, or hemisuccinate provides the desired compounds.

Where an exocyclic amine or protected amine is desired in the product, it can be introduced at any of several stages. For example, the starting pteridine may contain an amine substituent which is protected prior to further manipulation (e.g. see compounds of formula III). Alternatively, an amine may be introduced at a later stage by conversion of an oxo moiety to a thione followed by amination with ammonia (e.g. see Example 8 describing the synthesis of a phosphoramidite of formula VIII). Yet another method for introducing an amine uses a starting pteridine bearing a methylthio substituent in the 2 position (e.g. see Example 7 describing the synthesis of a phosphoramidite of formula V). After coupling with the desired chlorofuranose the protecting groups are removed and the methylthio group is displaced with ammonia.

The 5'-hydroxyl of the nucleoside is blocked with a protecting group (preferably dimethoxytrityl). Means of coupling protecting groups are well known to those of skill in the art. In particular, the coupling of a dimethoxytrityl group is illustrated in Examples 6 through 9. Briefly, this is accomplished by reaction of the nucleoside with dimethoxytrityl chloride in dry pyridine. Other protocols are generally known to those of skill in the art. See, for example, Atkinson et al., chapter 3, in Gait, ed., *Oligonucleotide Synthesis: A Practical Approach* (IRL Press, Washington, D.C., 1984), which is incorporated herein by reference.

The 3'-hydroxyl of the pteridine nucleoside can be converted to its respective hemisuccinate (for coupling to CPG as describe earlier), phosphoramidite, H-phosphonate, or triphosphate using methods well known to those of skill in the art. For example, conversion of the nucleoside 3'-hydroxyl to a hemisuccinate may be accomplished by reaction with succinic anhydride. Atkinson et al., chapter 3, in Gait, ed., *Oligonucleotide Synthesis: A Practical Approach* (IRL Press, Washington, D.C., 1984) which is incorporated herein by reference describe the functionalization of control pore glass and the synthesis and coupling of nucleoside-3'-O succinates.

Means of convening a nucleoside to a phosphoramidite are also well known to those of skill in the art. See, for example, Atkinson et al., chapter 3, in Gait, ed., *Oligonucleotide Synthesis: A Practical Approach* (IRL Press, Washington, D.C., 1984), which is incorporated herein by reference, who utilize the method of McBride and Caruthers, *Tetrahedron Lett.*, 24: 245 (1983). Another approach is illustrated in Examples 7 and 8 in which the nucleoside is reacted with β-cyanoethoxy-bis-diisopropylphosphane in tetrazole. Subsequent isolation of the phosphoramidite is described in those examples.

Similarly, means of convening a nucleoside to an H-phosphonate are also well known to those of skill in the art. In one approach, phosphorous (III) trichloride derivatives are used to directly phosphitylate the 3'-hydroxyl of the nucleoside. More specifically, phosphorous (III) triimidazolide may be used to phosphitylate the 3'-hydroxyl. This method is described in detail by Garegg et al. Chemica Scripta, 25: 280–282 (1985) and by Tocik et al. *Nucleic Acids Res.*, 18: 193 (1987) both of which are incorporated herein by reference. Similarly, the use of tris-(1,1,1,3,3,3-hexafluoro-2-propyl) phosphite to produce ribonucleoside-H-phosphonates is described by Sakatsume et al. *Nucleic Acids Res.*, 17: 3689–3697 (1989), which is incorporated herein by reference. The use of the same reagent to produce deoxynucleoside-H-phosphonates is described by Sakatsume et al. *Nucleic Acids Res.*, 18: 3327–3331 (1990), which is incorporated herein by reference. Other approaches to the derivatization of the 3'-hydroxyl to produce H-phosphonates may be found in Sekine et al. *J. Org. Chem.*, 47: 571–573 (1982); Marugg et al. *Tetrahedron Lett.*, 23: 2661–2664 (1986), and Pon et al. *Tetrahedron Lett.*, 26: 2525–2528 (1985).

Derivatization of the 3'-hydroxyl as a triphosphate may be accomplished by a number of means known to those of skill in the art. Where the pteridine nucleoside has sufficient structural similarity to native nucleotides to act as an enzymatic substrate, the monophosphate may be synthesized chemically as described below and then enzymatically converted to the diphosphate and then to the triphosphate using the appropriate nucleotide monophosphate and diphosphate kinases respectively.

Alternatively, the nucleoside may be chemically derivatized as the triphosphate. This may be accomplished by reacting the nucleoside with trimethyl phosphate and $POCl_3$ and then adding a triethylammonium bicarbonate buffer to form the nucleotide monophosphate which may then be purified chromatographically. The nucleotide monophosphate is then activated using carbonyldiimidazole and coupled with tributylammonium pyrophosphate to form the nucleotide triphosphate. The nucleotide triphosphate may then be precipitated as a sodium salt which is more stable than the trierthyklammonium salt and can be stored without decomposition. Details of the derivatization of a nucleoside to the nucleotide triphosphate are provided in Example 10.

The syntheses of the pteridine derivatives of the present invention are described in detail in the examples. In particular, the syntheses of pteridine nucleosides of formulas III, VI, IX, X and XI are illustrated in Examples 1 through 5 respectively. The syntheses of the pteridine nucleotide phosphoramidites of formulas IV, V, VIII and VII are illustrated in Examples 6, through 9. The conversion of pteridine nucleosides to pteridine nucleotide triphosphates is illustrated in Example 10. The synthesis, cleavage and deprotection of deoxyoligonucleotides incorporating one of the claimed pteridine nucleotides is illustrated in Example 11. Finally, the use of the claimed oligonucleotides in an assay for integrase activity is illustrated in Example 12. The examples are provided to illustrate, but not to limit the claimed invention.

EXAMPLE 1

Synthesis a Nucleoside of Formula III: 4-Amino-2-phenyl-8-(2-deoxy-β-D-ribofuranosyl)-pteridine-7-one (5).

a) Silver Salt of isonitrosomalononitrile (1)

Synthesis of the silver salt of isonitrosomalononitrile used in step (b) was described by Longo, *Gazz. Chim. Ital.,* 61: 575 (1931). To 120 mL of a solution of acetic acid and $H_2O$ (1/1) was added 20 g (0.3 mole) of malononitrile (Fluka, A G, Switzerland). The mixture was heated and stirred until the malononitrile dissolved. The mixture was then cooled to 0° C. and a solution of 23 g (0.33 mole) sodium nitrite in 100 mL of $H_2O$ was slowly added while stirring. The solution was then stirred at room temperature for 12 hours in the dark. To this orange colored solution was added a solution of 52 g (0.3 mole) of silver nitrate dissolved in 100 mL of $H_2O$. The resulting precipitate was collected, filtered under low vacuum, washed with ether and then dried in a desiccator over $P_4O_{10}$ in vacuum to yield 1 as 59.7 g (99% yield, m.p. >350° C.).

b) 2-phenyl-4,6-diamino-5-nitrosopyrimidine (2)

The synthesis of 2-phenyl-4,6-diamino-5-nitrosopyrimidine was described by Taylor et al., *J. Am. Chem. Soc.,* 81: 2442–2448 (1959). Small portions, 0.11 mole, of finely divided silver salt of isonitrosomalononitrile (1) was added to a stirred solution of 0.1 mole of benzamidine hydrohalide in 100 mL of methanol. Stirring was continued for one hour after addition was complete. By this time, the yellow silver salt had disappeared and a heavy precipitate of white silver halide had separated. The reaction mixture was filtered, and the yellow filtrate was evaporated at room temperature under reduced pressure to dryness. The yield of crude product was almost quantitative. Recrystallization from ethyl acetate yielded a pure benzamidine salt of isonitrosomalononitrile in the form of light yellow crystals (m.p. 151° C.–152° C.).

Analysis for $C_{10}H_5N_5O$ calculated: C, 55.8; H, 4.2; N, 32.5. Found: C, 55.7; H, 4.0; N, 32.6.

A mixture of 2 grams of the benzamidine salt of isonitrosomalononitrile in 10 mL of α-picoline was heated was heated to 125° to 130° C. for 0.5 hours. The salt dissolved rapidly and the color of the mixture gradually turned green. The reaction mixture was then cooled and diluted with $H_2O$. Filtration after standing yielded 2 as bluish green crystals of 2-phenyl-5,6-diamino-5-nitrosopyrimidine (m.p. 243°–244° C.).

Analysis for $C_{10}H_9N_5O$ calculated: C, 55.8; H, 4.2; N, 32.5. Found: C, 55.9; H, 3.9; N, 32.6.

c) 4-amino-2-phenyl-pteridine-7-one (3)

Synthesis of 4-amino-2-phenyl-pteridine-7-one was described by Harris et al., *Liebigs. Ann. Chem.* 1457–1468 (1981). To 200 mL of methanol was added 2.15 g (10 mmol)of 2-phenyl-4,6-diamino-5-nitrosopyrimidine (2). The mixture was hydrated in an agitator at room temperature using hydrogen via 5 % Pd/C-catalyst until the reaction ceased (approximately 2 hours). The colorless solution was filtered, combined with a solution of 1 g Na in 20 mL of $H_2O$, heated to a boil, and then treated with activated charcoal and filtered while hot. The filtrate was brought to pH 5 with glacial acetic acid and left to stand and cool. The precipitate was recrystallized from dimethylformamide to obtain 3 as 1.0 g of brownish crystals (42% yield, m.p. 330°–332° C.).

d) 4-Amino-2-phenyl-8-[2-deoxy-3,5-di-O-(4-chlorobenzoyl)-β-D-ribofuranosyl]-pteridine-7-one (4)

A mixture of 1.0 g (4.2 mmol) of 4-amino-2-phenyl-pteridine-7-one (3) and a few crystals of ammonium sulfate was heated in 100 mL of hexamethyldisilazane (HMDS) under reflux for 4 hours. After cooling the excess HMDS was distilled off in vacuum and the residue dissolved in 100 mL of dry toluene. To the mixture was added 2.17 g (4.6 mmol) of 2-deoxy-3,5-di-O-(4-chlorobenzoyl)-α-D-ribofuranosyl chloride (made as in Example 3, step (a) for the toluyl derivative) and 0.476 g (2.3 mmol) of silver perchlorate. The solution was then stirred under anhydrous conditions for 24 hours at room temperature and then diluted with 200 mL of $CH_2Cl_2$. The resulting AgCl precipitate was filtered off through silica and then the filtrate was treated with 100 mL of a saturated aqueous solution of sodium bicarbonate followed by 100 mL of a saturated aqueous solution of NaCl. The organic layer was dried over $Na_2SO_4$, filtered and then the filtrate evaporated.

The residue was dissolved in a little ethyl acetate, put onto a silica-gel column and then eluted with n-hexane / ethyl acetate 5:1. The main fraction was collected, evaporated and the residue recrystallized twice from $CHCl_3$/ methanol to give 4 as 1.43 g (54% yield) of colorless crystals (m.p. 175°–178° C.).

Analysis calculated for $C_{31}H_{23}Cl_2N_5O_6$ (632.5): C, 58.87; H, 3.67; N, 11.07. Found: C, 58.62; H, 3.74; N, 11.10.

e) 4-Amino-2-phenyl-8-(2-deoxy-β-D-ribofuranosyl)-pteridine-7-one (5)

To a solution of 10 mg of sodium in 50 mL of anhydrous methanol was added 0.632 g (1 mmol) of 4-amino-2-phenyl-8-[2-deoxy-3,5-di-O-(4-chlorophenyl)-βD-ribofuranosyl] pteridine-7-one (4). The solution was stirred at room temperature for 1 hour. The solution was then neutralized by the addition of AcOH and then evaporated. The residue was recrystallized from methanol / $H_2O$ to give 5 as 0.323 g (91% yield) of colorless crystals (m.p. 169°–172° C.).

Analysis calculated for $C_{17}H_{17}N_5O_4$ (355.4): C, 57.46; H, 4.81; N, 19.71. Found: C, 57.04; H, 4.88; N, 20.01.

EXAMPLE 2

Synthesis of a Nucleoside of Formula VI: 2'-Deoxy-β-D-ribofuranosylisoxanthopterin (15).

The synthesis of 2,4,5-triamino-6-benzyloxy-pyrimidine (9), steps (a) through (d), is described by Pfleiderer et al., Chem. Ber., 94: 12–18 (1961).

a) 6-chloro-2,4-diamino-pyrimidine (6)

To 500 mL of freshly distilled $POCl_3$ at a temperature of 80–90° C. is added 100 g of 2,4-diamino-6-oxo-dihydropyrimidine (Aldrich, Milwaukee, Wis., USA). The mixture is distilled under reflux until, after approximately 2 hours, the mixture has completely dissolved. The residual $POCl_3$ is suctioned off using vacuum and the remaining syrup is dripped slowly onto ice. The highly acidic solution is carefully neutralized by cooling it using concentrated sodium aluminate solution, and in the final stage with solid sodium carbonate. When completed the total volume of solution is approximately 1800 mL. Upon cooling a yellowish precipitate is separated out which is suctioned off and dried in a vacuum desiccator. The end product which contains mostly non-organic-salts is boiled three times, each time with 1 liter of acetone to which active charcoal is added. The extracts are cooled and the resulting clear precipitate is collected. Evaporation of the filtrates yields an additional fraction.

b) 2,4-diamino-6-benzyloxy-pyrimidine (7)

A solution of 3.8 g sodium in 100 mL benzylalcohol is heated in an oil bath with 21.6 g 6-chloro-2,4-diamino-pyrimidine (6) for 3 hours at 160° C. The surplus alcohol is distilled off in vacuum.

a) The oily residue is thoroughly washed in warm water thereby giving rise to a rubbery substance. The warm solution is dissolved in warm 30% acetic acid, faded with activated charcoal and brought to pH 6 using diluted ammonia. When slowly cooled an oily mass initially separates out, followed by a crystalline substance. The crystals are separated from the congealed oil by means of excitation, decanting and filtration. The oily residue is then heated and cooled several times to become crystalline. The pooled fractions, once they are dried in a vacuum desiccator, are dissolved in a small quantity of chloroform, then treated with activated charcoal and aluminum oxide (base, cationotropic $Al_2O_3$) and separated out again by intense freezing a temperature of −20° C. or lower. Several repetitions of this process yield chromatographically pure 7.

b) In an alternative purification process the alcohol-free reaction residue is dissolved in benzole, treated with activated charcoal and the filtrate is thoroughly evaporated. The product which separates out when cooled is recrystallized several times from benzole to yield 7.

c) 5-nitroso-2,4-diamino-6-benzyloxy-primidine (8)

To a solution of 16 g 2,4-diamino-6-benzyloxy-pyrimidine (7) in 250 mL of warm 30% acetic acid is added a solution of 7 g sodium nitrite in 25 mL $H_2O$. The sodium nitrite solution is held at 70°–80° C. and is added dropwise while being stirred continuously. The sodium nitrite solution is added until potassium-iodate starch paper shows a positive reaction. The violet-red precipitate is cooled, suctioned off and then recrystallized from ethanol or acetone to yield 8.

d) 2,4,5-triamino-6-benzyloxy-pyrimidine (9)

Sodium dithionite is added in portions to a suspension of 17 g 5-nitroso-2,4-diamino-6-benzyloxy-primidine (8) in 300 mL $H_2O$ at 50° C. until the red nitroso compound is fully reduced. The free base is separated out by adding aqueous ammonia. The crude product is cooled, suctioned off and crystallized from water, to which activated charcoal and a trace of sodium dithionite is added yielding 9.

e) 2,4-diamino-6-benzyloxy-5-ethoxycarbonylmethyleneimino-pyrimidine (10)

The synthesis of 2,4-diamino-6-benzyloxy-5-ethoxycarbonylmethyleneimino-pyrimidine is described by Pfleiderer & Reisser, Chem. Ber., 95: 1621–1628 (1961). A suspension of 2.3 g of 2,4,5-triamino-6-benzyloxy-pyrimidine (9) in 250 mL of $H_2O$ is agitated in 3 g ethylglyoxylate-hemiethylacetal for three hours at room temperature. The resulting bright yellow precipitate is filtered off under light vacuum, washed, and dried at a temperature of 100° C. The precipitate is recrystallized from ethanol to give 10.

f) 2-amino-4-benzyloxypteridine-7-one (11)

The synthesis of 2-amino-4-benzyloxypteridine-7-one is described by Pfleiderer & Reisser, Chem. Ber., 95: 1621–1628 (1961). To a solution of 1 g 2,4-diamino-6-benzyloxy-5-ethoxycarbonylmethyleneimino-pyrimidine (10) in 190 mL of ethanol is added 30 mL 1N $NaHCO_3$. The solution is distilled under reflux for 1 hour and then the solution is heat separated from the little remaining undissolved material. The pteridine that precipitates out due to acidification of the filtrate with 20 mL of glacial acetic acid is suctioned off after cooling and recrystallized from benzylalcohol to give 11.

g) 4-benzyloxy-2-(N,N-dimethylaminomethylenimino)-pteridine-7-one (12)

To 100 mL of anhydrous DMF is added 2.88 g (10.7 mmoles) of 2-amino-4-benzyloxypteridine-7-one (11) and 1.92 mL (11.2 mmoles) of N,N-dimethylforamidediethylacetal. The mixture is stirred at room temperature for 4 hours by which time it becomes a clear solution. The DMF is distilled off in high vacuum below 50° C. To the residue is then added a solution of 1 mL of methanol and 50 mL of diethylether. After 10 minutes, the precipitate is collected. The filtrate is again evaporated to dryness and the resulting residue is stirred in 10 mL of diethylether to yield a second precipitate. The precipitates are pooled and dried under high vacuum to give 12.

h) 4-benzyloxy-2-(N,N-dimethylaminomethyleneimino)-8-(2-deoxy-3,5-di-p-toluoyl-β-D-ribofuranosyl)-pteridine-7-one (13)

To 3.24 g (10 mmoles) of 4-benzyloxy-2-(N,N-dimethylaminomethyleneimino)-pteridine-7-one (12) is added 100 mL of anhydrous acetonitrile. Then 1.87 mL (12.5 mmoles) of DBU are added and the solution is stirred until it becomes clear after about 10 min. To this solution is gradually added 4.5 g (11 mmoles of 1-chloro-2-deoxy-3,5-di-O-p-toluoyl-α-D-ribofuranose. The stirring is then continued for 30 min. The resulting precipitate is collected to give after drying an α,β-anomeric mixture. The filtrate is evaporated to dryness, the residue dissolved in 100 mL of $CH_2Cl_2$ and twice washed with $H_2O$ to remove the DBU. The organic layer is dried over $Na_2SO_4$ and then evaporated. The resulting residue is purified by silica-gel column chromatography in toluene/ethyl acetate 1/3. The main fraction is collected and gives on evaporation an α,β-anomeric mixture. Both crops are pooled and recrystallized from ethyl acetate/methanol 20/1 to give 13.

i) 8-(2-Deoxy-3,5-di-O-p-toluoyl-β-D-ribofuranosyl)-isoxanthopterin (14)

In 100 mL of methanol are dissolved 3.38 g (5 mmoles) of 4-benzyloxy-2-(N,N-dimethylaminomethyleneimino)-8-(2-deoxy-3,5-di-p-toluoyl-βD-ribofuranosyl)-pteridine-7-one (13). Then 0.2 g of palladium-charcoal (5 %) is added and the mixture is shaken under hydrogen atmosphere for 1 day. The catalyst is faltered off and the filtrate evaporated to dryness. The residue is recrystallized from methanol to give 14.

j) 8-(2-Deoxy-β-D-ribofuranosyl)-isoxanthopterin (15)

To 30 mL of a saturated solution of ammonia in methanol is added 1.0 g (2 mmoles) of 8-(2-deoxy-3,5-di-O-p-toluoyl-β-D-ribofuranosyl)-isoxanthopterin (14). The mixture is stirred at room temperature overnight. The solution is then evaporated to dryness and the residue recrystallized from a little $H_2O$ by addition of drops of acetic acid. Cooling produces 15.

EXAMPLE 3

Synthesis of a Nucleoside of Formula IX: 4-Amino-1-(2-deoxy-β-D-ribofuranosyl)-7-methyl-pteridine-2-one (23).

a) 2-deoxy-3,5-di-O-p-toluoyl-α-D-ribofuranosyl-chloride (16)

The synthesis of 2-deoxy-3,5-di-O-p-toluoyl-α-D-ribofuranosyl chloride, used in step (e) is described by Hoffer, *Chem. Ber.*, 93: 2777–2781 (1960). To 243 mL of methanol is added 13.6 g (0.1 mol) of 2-deoxy-D-ribose (Aldrich, Milwaukee, Wis., USA) and 27 mL of 1% methanolized HCl. The mixture is allowed to stand sealed for 12–15 minutes to form methylglycoside. Afterwards, 3–5 g silver carbonate is mixed in to immediately bind all hydrogen chloride. The clear filtered solution is boiled down in vacuum to a syrup-like consistency and the remaining methanol is separated off by repeated boiling in vacuum while adding small amounts of dry pyridine. Finally the mixture is dissolved in 80 mL pyridine and acylated with 34 g (0.22 mole) p-toluylchloride while cooling. The mixture is then heated for two hours at 40°–50° C. or is allowed to stand overnight at room temperature. Water is added, after which the mixture is partitioned with 200 mL ether. The ether solution is then washed free of pyridine using $H_2O$ followed by dilute sulphuric acid followed by potassium hydrogen carbonate solution. The mixture is then boiled down in vacuum to form a honey-yellow syrup. From this syrup, it is possible to obtain crystallized 3,5-di-p-toluyl-methyl-2-deoxy-D-ribofuranoside by seeding.

To isolate the chloride, the syrup is dissolved in 20–50 mL glacial acetic acid and the solution is placed in a beaker together with 80 mL of acetic acid that has been saturated with hydrogen chloride. The solution is held at 10° C. and hydrogen chloride is introduced until the mixture hardens after about 10 minutes to a thick crystalline paste. After not more than 30 minutes, the crystalline substance is washed on a filter under low vacuum with absolute ether. This washing step is preferably repeated a second time. The substance is then dried in a vacuum desiccator with soda lime and phosphorous pentaoxide and remains stable in this condition for weeks. When desired, 2-deoxy-3,5-di-O-p-toluoyl-α-D-ribofuranosyl-chloride (16) is recrystallized from toluene or carbon tetrachloride.

b) 2-hydroxy-4,6-diaminopyrimidine sulfate (17)

The synthesis of 4,6-diamino-2-hydroxy-pyrimidine sulfate is described by Bendich et al. *J. Amer. Chem. Soc.*, 70: 3109–3113 (1948). To 5.40 g of 4,6-diamino-2-thiolpyrimidine (Aldrich Chemical Co., Milwaukee, Wis., USA) and 5.5 g of chloroacetic acid is added 75 mL of boiling $H_2O$. The solution is refluxed for 1.25 hours. Without cooling, 9.5 ml of 18N sulfuric acid is added and the refluxing is continued for an additional hour. Norite is added and upon cooling the filtrate yields 17.

c) 4,6-diamino-5-formylamino-2-hydroxy-pyrimidine (18)

The synthesis of 4,6-diamino-5-formylamino-2-hydroxy-pyrimidine is described by Pfleiderer, *Chem. Ber.* 90: 2272–2276 (1957). To 54 mL of formamide is added 9 g of 4,6-diamino-2-hydroxy-pyrimidine sulfate (17) and 4.5 g of sodium nitrite. This solution is heated to 60° C. and 10 mL of formic acid is added drop-wise. This forms a red suspension which is further heated to 110° C. Small quantities of sodium dithionite are added until a yellow coloring is obtained. During this time the temperature must not exceed 130° C. The mixture is allowed to cool and the precipitate is filtered off under light vacuum. Finally, 18 is recrystallized from a large amount of $H_2O$ with animal charcoal.

d) 4,5,6-triamino-pyrimidine-2-one hydrochloride (19)

The synthesis of 4,5,6-triamino-pyrimidine-2-one hydrochloride is described by Pfleiderer, *Chem. Ber.* 90: 2272–2276 (1957). To 3 g of 4,6-diamino-5-formylamino-2-hydroxy-pyrimidine (18) is added 50 mL of 10% to 15 % methanolic HCl. The solution is refluxed for 7 hours and then allowed to cool. Once cooled, the mixture is filtered under light vacuum, then washed in alcohol and dried in a drying chamber. The hydrochloride is then dissolved in $H_2O$ at room temperature and neutralized to pH 7 by the addition of 1N ammonia. The resulting precipitate is collected, washed with ethanol, and dried in a drying chamber to yield 19.

e) 4-amino-7-methyl-pteridine-2-one (20)

In 50 mL of $H_2O$ is dissolved 1.77 g (0.01 mole) of 4,5,6-triaminopyrimidine-2-one hydrochloride (19). The pH of the solution is adjusted to 5 and then, 4 mL of 40% aqueous methylglyoxal (FLUKA, A G, Switzerland) is added and the solution is heated under reflux for 30 minutes. The resulting precipitate is collected and purified by recrystallization from a large amount of $H_2O$ to give 20.

f) 4-benzoylamino-7-methyl-pteridine-2-one (21)

In 20 mL of pyridine is dissolved 1.63 g (0.01 mole) of 4-amino-7-methyl-pteridine-2-one (20). Then 3.12 g (0.02 mole) of benzoyl chloride is added dropwise while stirring the mixture. The mixture is heated to 80° C. for 30 minutes and then poured on ice. The resulting precipitate is collected, washed with ethanol and ether and then recrystallized from DMF to give 21.

g) 4-benzoylamino-1(2-deoxy-3,5-di-O-p-toluoyl-β-D-ribofuranosyl)-7-methyl-pteridine-2-one (22)

To 60 mL of anhydrous acetonitrile is added 2.83 g (0.01 mole) of 4-benzoylamino-7-methyl-pteridine-2-one (21). Then 1.5 mL (11 mmole) of 1,8-diazabicyclo[5.4.0]-undec-7-ene (DBU) is added and the mixture is stirred for 15 min at room temperature. After stirring, 4.26 g (11 mmole) of 2-deoxy-3,5-di-O-p-toluoyl-α-D-ribofuranosyl chloride is added to the solution and stirred for 1 hour at room temperature. The solution is then evaporated to dryness, the residue dissolved in $CHCl_3$, washed with sodium bicarbonate solution and the organic phase is dried over $Na_2SO_4$. After concentration to a small volume the material is purified by silica-gel column chromatography in ethyl acetate / acetone 4/1. The main fraction is evaporated and the residue recrystallized from ethanol to give 22.

h) 4-amino-1(2-deoxy-β-D-ribofuranosyl)-7-methyl-pteridine-2-one (23)

To 50 mL of saturated methanolic ammonia is added 1.65 g (0.005 mole) of 4-benzoylamino-1-(2-deoxy-3,5-di-O-p- toluoyl-β-D-ribofuranosyl)-7-methyl-pteridine-2-one (22). The mixture is stirred overnight at room temperature. The mixture is then evaporated to dryness and the residue recrystallized from ethanol/H$_2$O 20:1 to give 23.

EXAMPLE 4

Synthesis of a Nucleoside of Formula X: 4-Amino-1-(2-deoxy-β-D-ribofuranosyl)-6-methyl-pteridine-2-one (28).

a) methylglyoxalmonoaldoxime (24)

Methylglyoxalmonoaldoxime may be synthesized according to the protocol of G. Charrier Gazz. Chin:. Italy 37: 145 (1907). To 30 mL of an acetic acid/H$_2$O solution (1/1) is added 5.8 g (0.1 mole) of acetone. The solution is then cooled to 0° C. A solution of 7.6 g (0.11 mole) of sodium nitrite in 20 mL of H$_2$O is added dropwise with stirring. The solution is then stirred for another 3 hours at room temperature and then evaporated carefully in vacuum. The residue is extracted with benzene to give, on partial evaporation, 24 as colorless crystals. The crystals can be further purified by sublimation in high vacuum.

b) 4-Amino-6-methyl-pteridine-2-one (25)

To 50 mL of H$_2$O is added 1.77 g (0.01 mole) of 4,5,6-triaminopyrimidine-2-one hydrochloride (19) (see Example 3). The pH is adjusted to 5 and 1.74 g (0.02 mole) of methylglyoxalmonoaldoxime (24) is added while stirring the mixture. The resulting precipitate of the corresponding Schiff's base is collected, then dissolved in 25 mL of 80% sulfuric acid and heated to 100° for 30 min. After cooling the mixture is poured onto ice and then carefully neutralized by NaHCO$_3$ which results in the formation of a precipitate. The product is filtered and then recrystallized from a large volume of H$_2$O to give 25.

c) 4-benzoylamino-6-methyl-pteridine-2-one (26)

The synthesis of 4-benzoylamino-6-methyl-pteridine-2-one is carried out as in Example 3, step (d), substituting 4-amino-6-methyl-pteridine-2-one (25) for 4-amino-7-methyl-pteridine-2-one (20).

d) 4-benzoylamino-1-(-2-deoxy-3,5-di-O-p-toluoyl-β-D-ribofuranosyl)-6-methyl-pteridine-2-one (27)

The synthesis of 4-benzoylamino-1-(-2-deoxy-3,5-di-O-p-toluoyl-β-D-ribofuranosyl)-6-methylpteridine-2-one is carried out as in Example 3, step (e), substituting 4-benzoylamino-6-methyl-pteridine-2-one (26) for 4-benzoylamino-7-methyl-pteridine-2-one (21).

e) 4-amino-1-(2-deoxy-β-D-ribofuranosyl)-6-methyl-pteridine-2-one (28)

The synthesis of 4-Amino-1-(2-deoxy-β-D-ribofuranosyl)-6-methyl-pteridine-2-one is carried out as in Example 3, step (f), substituting 4-benzoylamino-1-(-2-deoxy-3,5-di-O-p-toluoyl-β-D-ribofuranosyl)-6-methylpteridine-2-one(27) for 4-benzoylamino-1-(-2-deoxy-3,5-di-O-p-toluoyl-β-D-ribofuranosyl)-7-methylpteridine-2-one (22).

EXAMPLE 5

Synthesis of a Nucleoside of Formula XI: 4-Amino-1-(2-deoxy-β-D-ribofuranosyl)-pteridine-2-one (32).

a) 4,5,6-triamino-2-hydroxypyrimidine sulfate (29)

Compound 17, 4,6-diamino-2-hydroxy-pyrimidine sulfate, is synthesized as described in Example 3 step (b). The conversion of 17 to 4,5,6-triamino-2-hydroxypyrimidine sulfate (29) is described by Bendich et al., *J. Amer. Chem. Soc.*, 70: 3109–3113 (1948). To a mixture of 110 mL of glacial acetic acid and 110 mL of H$_2$O is added 15.3 g of very finely pulverized 17. The mixture is kept at about 5° C. and 11.0 g of sodium nitrite in 25 mL of H$_2$O is added with constant stirring. The carmine red-colored precipitate is collected after two hours and washed with three small portions of chilled H$_2$O. The moist precipitate is suspended in 400 mL of H$_2$O and 45 g of sodium hydrosulfite is added and the mixture is boiled for three minutes during which time the substance is bleached. To this solution 53 mL of 18N sulfuric acid is carefully added. The fixture is boiled for a few minutes and filtered after Norite treatment to yield, on chilling 29 which can be recrystallized from 2N sulfuric acid.

b) 4-amino-pteridine-2-one (30).

The synthesis of 4-amino-pteridine-2-one is described by Taylor et al., *J. Amer. Chem. Soc.*, 71: 2538–2541 (1949). To a solution of 2.0 g (0.0084 mole) of 4,5,6-triamino-2-hydroxypyrimidine sulfate (29) in 50 mL of H$_2$O adjusted to pH 5 with dilute NaOH is added 3.0 g (0.0113 mole) of glyoxal bisulfite. The reaction mixture is heated to boiling, the pH adjusted to 9 and the boiling is continued for fifteen minutes. After neutralization with dilute hydrochloric acid, cooling and filtering, the light tan solid is washed with H$_2$O followed by acetone and dried in vacuo. The solid is dissolved in hot 0.5N NaOH and then treated with Norite. The hot filtrate is then acidified with acetic acid. A final recrystallization from 0.5N acetic acid gives 30.

c) 4-amino-1-(2-deoxy-3,5-di-O-p-toluoyl-β-D-ribofuranosyl)-pteridine-2-one (31)

To 20 mL of hexamethyldisilazane (HMDS) is added 2.98 g (0.02 mole) of 4-amino-pteridine-2-one (30). The mixture is heated for 24 hours under reflux, with moisture excluded, to obtain a clear solution. The excess HMDS is removed under high vacuum to give 1-trimethylsilylamino-2-trimethylsilyloxy-pteridine as a viscous oil. The residue is dissolved in 200 mL of benzene and then 9.37 g (0.022 mole) of 2-deoxy-3,5-di-O-p-toluoyl-α-D-ribofuranosyl chloride, 4 g HgO, and 4 g HgBr$_2$ are added and the mixture is refluxed for 5 hours. After cooling, the precipitate is filtered off, the filtrate evaporated to dryness and the residue dissolved in 100 mL of CHCl$_3$. The solution is extracted twice with 100 mL of 20% KI. The organic layer is then dried over Na$_2$SO$_4$, again evaporated and the residue dissolved in a little ethyl acetate for silica-gel column chromatography with ethyl acetate / acetone 7:3. The first fraction contains excess sugar, the second fraction the α-anomer and last eluting fraction the β-deoxyriboside. Evaporation and recrystallization of the residue from ethanol gives 31.

d) 4-amino-1-(2-deoxy-β-D-ribofuranosyl)-pteridine-2-one (32)

To 0.51 g (1 mmole) of 4-amino-1-(2-deoxy-3,5-di-O-toluoyl-β-D-ribofuranosyl)-pteridine-2-one (31) is added 50 mL of 0.0005N sodium methoxide. The mixture is stirred at room temperature for 24 h. The mixture is then neutralized with AcOH, evaporated to dryness, and twice coevaporated with H$_2$O. The residue is then recrystallized from 50 mL of ethanol to give 32.

EXAMPLE 6

Synthesis of A Phosphoramidite of Nucleoside of Formula IV: 4-Amino-6-phenyl-8-(5-O-dimethoxytrityl-2-deoxy-β-D-ribofuranosyl)-pteridine-7-one-3'-O-(β-cyanoethyl, N-diisopropyl)phosphoramidite (41 )

The synthesis of 4,6-diamino-5-nitroso-pyrimidine, steps (a) through (c), was described by Evans et al. *J. Chem. Soc.*, 4106 (1956).

a) 4,6 diaminopyrimidine-2-sulphinic acid (33)

To a solution of 50 g of 4,6-diamino-2-mercaptopyrimidine (Aldrich, Milwaukee, Wis., USA) in 2N NaOH (220 mL) was added 750 mL of a 3% hydrogen peroxide solution.

The solution was maintained at a temperature less than 20° C. Stirring was continued for a further 30 minutes and the clear pale yellow solution was acidified with acetic acid (ca. 50 mL). The precipitate was washed with $H_2O$ and air dried, to give 33 as 58 g (95 % yield) of an off-white amorphous acid (m.p. 168°–170° C. decomp.). For analysis, a sample was dissolved in dilute aqueous ammonia and reprecipitated with acetic acid.

Analysis for $C_4H_6N_4O_2S$ calculated: C, 27.6; H, 3.5; N, 32.2. Found C, 27.8; H, 3.8; N, 32.2.

b) 4, 6-diamino-pyrimidine hydrochloride (34)

To 500 mL of dry ethanol containing 2.5N ethanolic hydrogen chloride (150 mL) was added 50 g of 4,6-diaminopyrimidine-2-sulphinic acid (33). The mixture was shaken for 30 minutes. The mixture was then cooled to 0° C. and, after 1 hour, the crystals were removed, washed with ether, and dried to give 23 g of pale yellow needles (m.p. 196°–198° C.). Concentration of the original filtrate to 250 mL, followed by addition of 750 mL of ether, gave a further crop of 15 g of almost white needles (m.p. 188° C.). Recrystallization from spirit gave 34 as white needles (m.p. 203°–204° C.). Analysis for $C_4H_6N_4.HCl$ calculated: C, 32.8; H, 4.8; N, 3.82; Cl, 24.2. Found C, 33.3; H, 4.8; N, 38.1; Cl, 24.1.

The sulphinic acid (5 g) was then added portion-wise to hydrochloric acid (15 ml; d 1.18) at room temperature. The reaction was vigorous and sulphur dioxide was freely evolved. Hydrochloric acid was removed from the resulting slurry under reduced pressure. The residue was washed with acetone and then ether to give 4.05 g of 7 (m.p. 195° C.). Recrystallization of a sample from spirit raised the melting point to 201°–202° C.

c) 4,6-diamino-5-nitroso-pyrimidine (35)

To 250 mL of 2N HCl was added 8.0 g (55 mmoles) of 4,6-diaminopyrimidine hydrochloride (34). The 4,6-diamino-pyrimidine hydrochloride was allowed to dissolve. The solution was then cooled to 0° C. and a solution of 4.2 g (61 mmoles) of $NaNO_2$ dissolved in 15 mL of $H_2O$ was added dropwise within 20 minutes while stirring. Stirring was continued for another 30 minutes at 0° and then 2 hours at room temperature. The violet solution was neutralized by $NaHCO_3$, the precipitate collected, washed with $H_2O$ and ethanol and dried to give 35 as 6.3 g (82 %) yield) of a blue-violet crystal powder (m.p. >350° C.).

d) 4-amino-6-phenyl-pteridine-7-one (36)

The synthesis of 4-amino-6-phenyl-pteridine-7-one was described by Harris et al., *Liebigs. Ann. Chem.* 1457–1468 (1981). To a solution of 0.5 g Na in 50 mL of absolute ethanol was added 1.38 g (10 nmol) of 4,6-diamino-5-nitroso-pyrimidine (35) and 2.0 g of phenyl acetic acid ethylester. The materials were allowed to dissolve and the solution was then heated for 1 hour under reflux. The precipitate which settled out was cooled and collected. The precipitate was then heated in 100 mL $H_2O$, filtered off from the insoluble nitroso compound, and then acidified to pH 2 using dilute hydrochloric acid. Once the gelatinous reaction product precipitated out it was heated until it reached a microcrystalline state. The gelatinous reaction product was then drawn off and recrystallized from dimethylformamide yielding 36 as crystals (m.p. >320° C.).

Analysis for $C_{12}H_9N_5O$ calculated: C, 60.24; H, 3.79; N, 29.28. Found C, 60.35; H, 3.78; N, 29.53.

e) 4-N,N-Dimethylaminomethyleneimino-6-phenyl-pteridine-7-one (37)

A mixture of 400 mL of dry DMF, 2.39 g (10 mmol) of 4-amino-6-phenyl-pteridine-7-one (36) and 2.5 mL of N,N-dimethylformamide-diethylacetal was stirred at 60° C. for 5 hours. The solution was evaporated in vacuum to dryness and the residue recrystallized from isopropanol to give 37 as 2.83 g (96% yield) of colorless crystals (m.p. 284°–286° C.).

Analysis calculated for $C_{15}H_{14}N_6O$ (294.3): C, 61.2 1; H, 4.79; N, 28.55. Found: C, 60.88; H, 5.00; N, 28.15.

f) 4-N,N-Dimethylaminomethyleneimino-6-phenyl-8-[2-deoxy-3,5-di-O-(4-chlorobenzoyl)-β-D-ribofuranosyl]pteridine-7-one (38)

To 60 mL of dry acetonitrile was added 2.94 g (10 mmol) of 4-N,N-dimethylaminomethyleneimino-6-phenyl-pteridine-7-one (37) and 1.49 mL (11 mmol)of 1,8-diazabicyclo [5.4.0]undec-7-ene (DBU). The solution was stirred for 15 min until clear. To this solution was added 4.72 g (11 mmol) of 2-deoxy-3,5-di-O-(4-chlorobenzoyl)-α-D-ribofuranosyl chloride (made as in Example 3, step (a) for the toluyl derivative). The solution was then stirred for 2 hours at room temperature during which period a yellowish precipitate formed. The solid precipitate was collected and recrystallized from $CHCl_3$/methanol to provide 38 as 5.3 g (83% yield) of yellowish crystals (m.p. 171°–174° C.).

Analysis calculated for $C_{34}H_{28}Cl_2N_6O_6$. ½ $H_2O$ (696.6): C, 58.62; H, 4.05; N, 12.06. Found: C, 58.71; H, 4.16; N 11.91.

g) 4-Amino-6-phenyl-8-(2-deoxy-β-D-ribofuranosyl)-pteridine-7-one (39)

To a solution consisting of 70 mg of $K_2CO_3$ in 25 mL of anhydrous methanol was added 0.687 g (1 mmol) of 4-N,N-dimethylaminomethylenimino-6-phenyl-8-[2-deoxy3,5-di-O-(4-chlorobenzoyl)-β-D-ribofuranosyl]pteridine-7-one (38). Then 0.7 mL of concentrated ammonia was added to this suspension. The solution was neutralized by the addition of AcOH after stirring for 2 days at room temperature and the resulting yellow precipitate (0.2 g, 56% yield) collected. The filtrate was evaporated to dryness and the residue recrystallized from methanol to give 39 as another 0.12 g (34% yield) of yellow crystals (m.p. 163° C. decomp.).

Analysis calculated for $C_{17}H_{17}N_5O_4$. ½ $H_2O$ (364.4): C, 56.03; H, 4.97; N, 19.22. Found: C, 56.16; H, 4.75; N, 19.14.

h) 4-Amino-6-phenyl-8-(5-O-dimethoxytrityl-2-deoxy-β-D-ribofuranosyl)-pteridine-7-one (40)

To a solution of 0.355 g (1 mmol) of 4-amino-6-phenyl-8-(2-deoxy-β-D-ribofuranosyl)-pteridine-7-one (39) in 10 ml of anhydrous pyridine were added some molecular sieves and 0.407 g (1.2 mmol) of dimethoxytrityl chloride. The solution was stirred at room temperature for 12 hours. The molecular sieves were filtered off and the filtrate evaporated. The residue was dissolved in 30 ml of $CH_2Cl_2$ then extracted with a saturated solution of $NaHCO_3$, followed by a saturated solution of NaCl. The organic layer was dried over $Na_2SO_4$, then evaporated again and the residue put onto a silica gel column for chromatography with toluene/EtOAc 1:1 as eluent. The product fraction was evaporated, dissolved again in little $CH_2Cl_2$ and then drop-wise added to n-hexane with stirring to give after drying in a vacuum desiccator 40 as 0.46 g (70%) of a yellowish crystal powder of m.p. 114° C. (decomp.).

Analysis calculated for $C_{38}H_{35}N_5O_6$ (657.7): C, 69.39; H, 5.36; N, 10.64. Found: C, 68.91; H, 5.67; N, 10.44.

i) 4-Amino-6-phenyl-8-(5-O-dimethoxytrityl-2-deoxy-β-D-ribofuranosyl)-pteridine-7-one-3'-O-(β-cyanoethyl, N-diisopropyl)phosphoramidite (41)

To a solution of 0.657 g (a mmol) of 4-amino-6-phenyl-8-(5-O-dimethoxytrityl-2-deoxy-β-D-ribofuranosyl)-pteridine-7-one (40) in 15 ml of $CH_2Cl_2$ were added 0.452 g (1.5 mmol) of 2-cyanoethoxy-bis-N,N-diisopropylamino-phosphane and 35 mg (0.5 mmol) of tetrazole. The mixture was then stirred under argon atmosphere for 12 hours at room temperature. The reaction solution was diluted with 15 ml of CH$_2$Cl$_2$ and then extracted with saturated solutions of NaHCO$_3$ and NaCl. The organic phase was dried over Na$_2$SO$_4$, filtered and evaporated. The residue was put onto a silica gel column for chromatography with toluene / EtOAc 3:2 containing a small amount of triethylamine. The product fraction was collected, evaporated, the residue dissolved in little toluene and then added dropwise to 100 ml of n-hexane with stirring to give 41 as 0.78 g (91%) of a microcrystalline powder (m.p. >100° C. decomp.).

Analysis calculated for C$_{47}$H$_{52}$N$_7$O$_7$P (858.0): C, 65.80; H, 6.11; N, 11.43. Found C, 66.13; H, 6.20; N, 11.03.

EXAMPLE 7

Synthesis of a Phosphoramidite of Formula V: (3-Methyl-8-(2-deoxy-5-O-dimethoxytrityl-β-D-ribofuranosyl)isoxanthopterin-3'-O-(β-cyanoethyl, N-diisopropyl)phosphoramidite) (51)

a) 2-methylmercapto-4-amino-6-oxo-pyrimidine (42)

The synthesis of 2-methylmercapto-4-amino-6-oxy-pyrimidine was described by Johns et al., *J. Biol. Chem.*, 14: 381–387 (1913). To 100 mL of a 10 percent solution of NaOH was added 25 g of pulverized 4-amino-2-mercapto-6-oxopyrimidine (Aldrich, Milwaukee, Wis., USA). To this solution was added 25 g of technical dimethylsulphate in small portions, with thorough shaking after each addition. In some cases it was found necessary to dilute the solution with H$_2$O as the precipitate which resulted became too thick to permit thorough mixing to take place. After the mixture had stood at room temperature for 15 minutes, it gave an acid reaction and the precipitate was filtered by suction. The mercapto pyrimidine thus obtained was removed to a flask while still moist, 200 mL of 95 percent alcohol were added and the mixture was heated to the boiling point of the alcohol. This dissolved most of the precipitate. The flask was then cooled and allowed to stand at room temperature for an hour. On filtering, 20 to 25 grams of pure 42 were obtained. This was 75 to 90% of the calculated weight.

b) 4-amino-1-methyl-2-methylthio-6-oxodihydropyrimidine (43)

The synthesis of 4-amino-1-methyl-2-methylthio-6-oxodihydropyrimidine was described by Johns et al., *J. Biol. Chem.*, 20: 153–160 (1915). To 65 mL of normal potassium hydroxide solution was added 10 g of 2-methylmercapto-4-amino-6-oxo-pyrimidine (42). To this solution was gradually added 9 grams of dimethyl sulphate while the solution was agitated by frequent shaking. A white, crystalline precipitate began to appear almost immediately, and this soon became very bulky. As soon as the solution became acid to litmus, the crystals were filtered off by suction. The filtrate was neutralized with NaOH, and evaporated to dryness. The residue was washed with cold water, the solid was filtered off and added to the crystals already obtained. The combined solids were then triturated with dilute ammonia to dissolve any unaltered 2-methylmercapto-4-amino-6-oxo-pyrimidine, a small quantity of which was found to be present. That part of the residue which was not soluble in ammonia consisted of two compounds which differed widely as to their melting points and solubility in ether. The compound having the lower melting point was very soluble in ether, while the one with the higher melting point was almost insoluble in this solvent. Ether, therefore, served as a means of separating these compounds from each other.

The compound soluble in ether was 2-methylmercapto-4-amino-6-methoxypyrimidine. This compound was removed from the solid residue by repeated washings with ether and filtering out of the solid residue. The solid residue was then recrystallized from alcohol to give 43 as slender prisms (yield=60%, m.p. 255° C.).

Analysis calculated for C$_6$H$_9$ON$_3$S: N, 24.57. Found N, 24.71.

c) 6-amino-3-methyl-2-methylthio-5-nitroso-pyrimidine-4-one (44)

The synthesis of 6-amino-3-methyl-2-methylthio-5-nitroso-pyrimidine-4-one (=4-amino-1-methyl-2-methylthio-5-nitroso-6-oxodihydropyrimidine)was described by Schneider et al. *Chem. Ber.*, 107: 3377–3394 (1974). To a suspension of 11 g of 4-amino-1-methyl-2-methylthio-6-oxodihydropyrimidine (43) in 1 L of 30% acetic acid was added dropwise a solution of 50 g of sodium nitrite in 100 mL of H$_2$O. The mixture was stirred for an additional hour at room temperature and then cooled in a refrigerator overnight. The precipitate was collected and washed with H$_2$O and then acetone and dried at 100° C. This yields 119.5 g (92% yield) of a chromatographically uniform crude product (m.p. 230° C. decomp.). Recrystallization of 1 g of this material from 240 mL of H$_2$O gave 44 as 0.52 g of blue crystals (m.p. 234° C. decomp.).

d) 5,6-Diamino-3-methyl-2-methylthio-pyrimidine-4-one (45)

To 4.0 g (0.02 mole) of 6-amino-3-methyl-2-methylthio-5-nitroso-pyrimidine-4-one (44) was added 40 mL of 20% aqueous ammonium sulfide solution. The mixture was heated under reflux for 30 min. After cooling the precipitate was collected, washed with a little ethanol and dried in a desiccator to give 45 as 2.72 g (75% yield) of colorless crystals (m.p. 211°–212° C.).

e) 1-methyl-2-methylmercapto-4-amino-6-oxo-dihydropyrimidine-azomethinecarbonic acid-5 ethylester (46).

The synthesis of 3-methyl-2-methylthio-pteridine-4,7-dione from 1-methyl-2-methylmercapto-4,5-diamino-6-oxo-dihydropyrimidine (5,6-diamino-3-methyl-2-methylthio-pyrimidine-4-one), steps c and d, was described by Pfleiderer, *Chem. Ber.* 91: 1670 (1958). In 200 mL of H$_2$O was dissolved 6 g of 5,6-diamino-3-methyl-2-methylthio-pyrimidine-4-one (45). The solution was cooled to room temperature and then combined with 6 g ethylglyoxylate-hemiethylacetal. The thick precipitate that immediately resulted was drawn off after one hour and recrystallized from ethanol producing 8 g of bright yellow crystals of 46 (m.p. 178° C.).

Analysis calculated for C$_{10}$H$_{14}$N$_4$O$_3$S.H$_2$O: C, 41.66; H, 5.59; N, 19.44. Found: C, 42.18; H, 5.57; N, 19.32.

f) 3-methyl-2-methylthio-pteridine-4,7-dione (47)

To 200 mL of 0.5N NaHCO$_3$ was added 8 g of 1-methyl-2-methylmercapto-4-amino-6-oxo-dihydropyrimidine-azomethinecarbonic acid-5 ethylester crystals (46). The solution was refluxed 30 minutes. The clear solution was treated with animal charcoal and then heat acidified to pH 1. Once cooled the precipitate was collected and recrystallized from H$_2$O yielding 47 as 4.5 g of faint yellow crystals of 3-methyl-2-methylthio-pteridine-4,7-dione (m.p. 292°–294° C.).

Analysis calculated for C$_8$H$_8$N$_4$O$_2$S: C, 42.86; H, 3.60; N, 24.99. Found: C, 42.70; H, 3.58; N, 24.43.

g) 3-Methyl-2-methylthio-8-[2-deoxy-3,5-di-O-(4t-chloro-β-D-ribofuranosyl]pteridine-4,7-dione (48)

Crystals of 3-methyl-2-methylthio-pteridine-4,7-dione (47) were dried in a drying oven at 100° C. under high vacuum. Then 5.6 g (25 mmol) of the dried crystals were suspended in 250 mL of anhydrous acetonitrile under argon atmosphere with 12.9 g of 2-deoxy-3,5-di-O-(4-chlorobenzoyl)-D-ribofuranosyl chloride (made as in Example 3, step (a) for the toluyl derivative). Then 3 mL of hexamethyldisilazane and 2 mL of trimethylsilyl chloride were added. The mixture was stirred for 30 minutes and then 7.4 mL of $SnCl_4$ was added dropwise within 2 minutes. After exactly 20 min of reaction the mixture was poured slowly into 1200 mL of a chilled saturated aqueous solution of sodium bicarbonate. The solution was then extracted three times with 200 mL of ethyl acetate each. The pooled organic layers were washed with a saturated solution of NACl, dried over $MgSO_4$, evaporated to dryness and coevaporated three times with $CH_2Cl_2$.

The resulting residue consisting mainly of an α, β anomeric nucleoside mixture was separated by fractional recrystallization. The first crystallization was done with 200 mL methanol/350 mL ethyl acetate. The resulting precipitate was again recrystallized from 200 mL methanol/280 mL ethyl acetate and then the resulting solid once more recrystallized from 200 mL methanol/500 mL ethyl acetate leading to 4.54 g of colorless crystals consisting of pure α-nucleoside (m.p. 188°–191 ° C., 29% yield). The filtrates were combined, evaporated, and the residue was recrystallized from 100 mL methanol/130 mL ethyl acetate yielding to 1.8 g of the α,β-mixture (12% yield). The filtrate thereof was again evaporated to dryness the residue was recrystallized from 50 mL ethyl acetate / 50 mL ether to yield 48 as 6.79 g (44% yield) of chromatographically pure crystalline β-nucleoside (m.p. 130°–133° C.).

Analysis calculated for $C_{27}H_{22}Cl_2N_4O_7S$: C, 52.52; H, 3.59; N, 9.07. Found: C, 52.45; H, 3.61; N 8.90.

h) 3-Methyl-8-(2-deoxy-β-D-ribofuranosyl)isoxanthopterin (2-Amino-3-methyl-8-(2-deoxy-β-D-ribofuranosyl)-pteridine-4,7-dione) (49)

A solution of 3.3 g (4 mmol) of 3-methyl-2-methylthio-8-[2-deoxy-3,5-di-O-(4-chlorobenzoyl)-β-D-ribofuranosyl] pteridine-4,7-dione (48) in 100 mL of dry acetonitrile was treated added to 100 mL of saturated methanic ammonia at room temperature. The mixture was let stand for 24 hours. A small amount of insoluble material was filtered off and the filtrate evaporate to dryness. After two coevaporations with methanol the precipitate was dissolved in 20 mL of warm methanol. Then 50 mL of ethyl ether was added and the mixture was chilled in the ice-box for 3 days. The precipitate was collected and dried at 60° C. in vacuum yielding 49 as 1.46 g (88% yield) of colorless crystals (m.p. >250° C. decomp.).

Analysis calculated for $C_{12}H_{15}N_5O_5.\frac{1}{2} H_2O$: C, 45.28; H, 5.07; N, 22.00. Found: C, 45.55; H, 5.07; N 21.92.

i) 3-Methyl-8-(2-deoxy-5-O-dimethoxytrityl-β-D-ribofuranosyl)isoxanthopterin (50)

To 3.1 g (10 mmol) of 3-methyl-8-(2-deoxy-β-D-ribofuranosyl)isoxanthopterin (49) was added 50 mL of dry pyridine. The solution was then coevaporated. The coevaporation was repeated three times with 50 mL of dry pyridine each. The residue was then suspended in 50 mL of dry pyridine. To this solution was added 5.1 g (15 mmol) of dimethoxytrityl chloride and the mixture was stirred at room temperature. After 10 minutes a clear solution was obtained and after 3 hours the reaction was stopped by addition of 10 mL of methanol. The solution was evaporated, the residue dissolved in $CH_2Cl_2$ and then extracted twice with a 5% aqueous solution of sodium bicarbonate. The organic layer was dried over $MgSO_4$ and the filtrate evaporated again. The residue was dissolved in a little $CH_2Cl_2$/methanol, put onto a silica-gel column (3×20 cm, packed with toluene / ethyl acetate) for flash-chromatography. A gradient of solvent mixtures had to be applied to achieve purification: 500 mL toluene/ethyl acetate 1:1, 2.5 l of ethyl acetate, 1 l of ethyl acetate/methanol 99:1 and 2 l of ethyl acetate/methanol 98:2. The substance fraction in ethyl acetate/methanol was evaporated and dried in high vacuum to give 50 as 3.9 g (63% yield)) of a colorless amorphous solid.

Analysis calculated for $C_{33}H_{33}N_5O_7.\frac{1}{2} H_2O$: C, 63.86; H, 5.52; N, 11.28. Found: C, 63.90; H, 5.82; N, 10.86.

j) 3-Methyl-8-(2-deoxy-5-O-dimethoxytrityl-β-D-ribofuranosyl)isoxanthopterin-3'-O-(β-cyanoethyl, N-diisopropyl)phosphoramidite (51)

A suspension of 3.06 g (4.9 mmol) of 3-methyl-8-(2-deoxy-5-O-dimethoxytrityl-β-D-ribofuranosyl)isoxanthopterin (50) and 0.18 g (25 mmol) of tetrazole was stirred under argon atmosphere with 2.2 g (7.3 mmol) of β-cyanoethoxy-bis-diisopropylphosphane. The suspension became clear after 30 min and the reaction was stopped after 4 hours. The reaction solution was extracted once with a 5% aqueous solution of sodium bicarbonate, then the organic layer was dried over $MgSO_4$ and the filtrate evaporated to dryness. Purification was done by flash-chromatography on a silica-gel column (3×20 cm) in 200 mL of hexane / ethyl acetate 2:1 followed by 2 l of hexane / ethyl acetate 1:1. The product fraction was collected, evaporated to dryness and dried in high vacuum to give 51 as 2.38 g (59% yield)) of a colorless amorphous solid.

Analysis calculated for $C_{42}H_{50}N_7O_8P . H_2O$ (820.8): C, 61.45; H, 6.26; N, 11.94. Found: C, 61.56; H, 6.47; N 11.51.

EXAMPLE 8

Synthesis of a Phosphoramidite of Formula VIII: (6,7-Dimethyl-4-[2-(4-nitrophenyl)ethoxycarbonyl)amino-1-(2-deoxy-5-O-dimethoxy-trityl-β-D-ribofuranosyl)-pteridine-2-one-3'-O-(β-cyanoethyl, N-diisopropyl)phosphoramidite (59).

a) 4,5-diaminouracil-hydrochloride (52)

The synthesis of 4,5-diaminouracil-hydrochloride, used in step (b) is described by Sherman & Taylor, Org. Syn. Coil. Vol IV, 247. In a 3 L, three-necked flask equipped with a reflux condenser and an efficient stirrer was placed 1 L of absolute (99.8%) ethanol. To this was added 39.4 g (1.72 g. atom) of sodium, and, after solution is complete, 91.5 mL (97.2 g., 0.86 mole) of ethyl cyanoacetate and 51.5 g (0.86 mole) of urea were added. The mixture was heated under reflux on a steam bath with vigorous stirring for 4 hours. After about 2 hours, the reaction mixture becomes practically solid, and the stirrer may have to be stopped. At the end of the reaction time, 1 L of hot (80° C.) $H_2O$ was added to the reaction mixture, and stirring is resumed. After complete solution has taken place, the stirred mixture was heated at 80° for 15 minutes and is then neutralized to litmus with glacial acetic acid. Additional glacial acetic acid (75 mL) was added, followed by cautious addition of a solution of 64.8 g (0.94 mole) of sodium nitrite dissolved in 70 mL of $H_2O$. The rose-red nitroso compound separated almost immediately as an expanded precipitate which almost stopped the stirrer. After a few minutes the nitroso compound was removed by filtration and washed twice with a small amount of ice water. The moist material was transferred back to the 3 L flask, and 430 mL of warm $H_2O$ (50° C.) were added.

The slurry was stirred while being heated on a steam bath, and solid sodium hydrosulfite was added until the red color of the nitroso compound was completely bleached. Then an additional 30 g of sodium hydrosulfite was added; the light tan suspension was stirred with heating for 15 minutes more and was allowed to cool. The dense diaminouracil bisulfite was filtered from the cooled solution, washed well with $H_2O$, and partially dried.

The crude product was readily purified by conversion to its hydrochloride salt. The bisulfite salt was transferred to a wide-mouthed 1-L flask, and concentrated hydrochloric acid was added until the consistency of the resulting mixture was such as to permit mechanical stirring (100 to 200 mL of acid). The slurry was heated on a steam bath with stirring for 1 hour. The tan diaminouracil hydrochloride was filtered on a sintered glass funnel, washed well with acetone, and vacuum-dried over phosphorus pentoxide to yield 104–124 g of 52 (68–81%).

b) 6,7-dimethyllumazine (53)

The synthesis of 6,7-dimethyllumazine is described by Pfleiderer et al. *Chem. Ber.*, 106: 3149–3174 (1973). To a solution consisting of 50 mL $H_2O$, 20 mL ethanol, and 1 mL concentrated HCl was added 20 mL of diacetyl. The solution was heated to a boil and droplets of a solution of 20 g 4,5-diaminouracil-hydrochloride (52) in 450 mL of $H_2O$ were slowly added. The mixture was heated under reflux for 2 hours, refrigerated in an ice box overnight and the resulting precipitate (18.7 g) was collected. The precipitate was purified by boiling it in 500 mL $H_2O$, to which a diluted sodium aluminate solution was added until the precipitate was dissolved. The solution was filtered through activated charcoal after which the filtrate was added dropwise into boiling, diluted acetic acid. After cooling, the mixture was dried at a temperature of 100 ° C. under reduced pressure to give 53 as 17.0 g (79% yield) of virtually colorless crystals (m.p. >360° C.).

c) 6,7-dimethyl-1-(2-deoxy-3,5-di-O-toluoyl-β-D-ribofuranosyl)lumazine (54)

The synthesis of 6,7-dimethyl-1-(2-deoxy-3,5-di-O-toluoyl-β-D-ribofuranosyl)lumazine is described by Ritzmann et al., *Liebigs Ann. Chem.*, 1217–1234 (1977). To 50 mL of hexamethyldisilazane was added 7.68 g of 6,7-dimethyllumazine (53) and a few ammonium sulfate crystals. The solution was heated under reflux for about 24 hours until it became clear. The excess hexamethyldisilazane was then distilled off in vacuum. The residue was dissolved in 220 mL of absolute benzole, 16 g of 3,5-Di-O-p-toluoyl-2-desoxy-d-erythro-pentofuranosylchloride was added and the solution was agitated for a period of one week at room temperature under dry conditions. To this solution was added 5 mL of methanol. The solution was evaporated to dryness, and the residue was recrystallized from 200 mL of methanol. Nearly DC-pure 6,7-Dimethyl-1-(2-deoxy-3-5-di-O-p-toluoyl-β-D-ribofuranosyl)-4-thiolumazine (the β isomer) was precipitated out. Renewed recrystallization of this first fraction from 300 mL methanol yielded 2.36 g of pure β isomer. The filtrates were purified, evaporated to dryness and then chromatographed over a silica gel column (70×5 cm) using chloroform/methanol (30:1 ). The first main fraction to appear yielded 6.5 g DC-pure 6,7-dimethyl-1-(2-deoxy-3-5-di-O-p-toluoyl-α-D-ribofuranosyl)-4-thiolumazine (the α isomer) after it was evaporated to a colorless amorphous solid. The subsequent mixed fraction was also evaporated to dryness, recrystallized from 100 mL methanol, after which an additional 2.67 g of colorless crystals of the 13 isomer were precipitated out with a melting point of 154°–155° C. The filtrate was again evaporated to dryness, poured on a silica gel column (900 g) and developed with chloroform/acetone (9:1). An additional 2.7 g of the α isomer was obtained from the main fraction having the greater $R_F$ value and an additional 0.43 g of the β isomer from the fraction with the lesser $R_F$ value. The total yield consisted of 54 as 5.46 g (25% ) of the β isomer in the form of colorless crystals with a melting point of 154°–155° C. and 9.2 g (43% yield) of the α isomer as an amorphous solid (m.p. 126°–132° C.). Note that the assignment of the α- and β-D-anomers was reversed after the Ritzman et al. paper by Cao et at., *Helv. Chim. Acta.*, 75: 1267–1273 (1992).

d) 6,7-Dimethyl-1-(2-deoxy-3-5-di-O-p-toluoyl-β-D-ribofuranosyl)-4-thiolumazine (55).

A mixture of 0.871 g (1.6 mmol) of 6.7-dimethyl-1-(2-deoxy-3,5-di-O-toluoyl-β-D-ribofuranosyl)lumazine (54) and 0.403 g (1 mmol) of Lawesson reagent in 20 mL of toluene was refluxed for 20 hours. The mixture was then evaporated, the residue taken up in 20 mL of $CH_2Cl_2$ and then treated twice with a saturated solution of sodium bicarbonate. The aqueous phase was extracted three times with 10 mL of $CH_2Cl_2$ each, the united organic extracts dried over $Na_2SO_4$, filtered and again evaporated. Recrystallization of the residue from 150 mL of methanol yielded 55 as 0.67 g (75% yield) of orange-colored crystals (m.p. 166°–168° C.).

Analysis calculated for $C_{29}H_{28}N_4O_6S \cdot H_2O$ (578.6): C, 60.20; H, 5.22; N, 9.68. Found: C, 60.43; H, 5.06; N 9.72.

e) 4-Amino-6,7-dimethyl-1-(2-deoxy-β-D-ribofuranosyl)-pteridine-2-one (56)

In an autoclave was heated 0.42 g (0.75 mmol) of 6,7-dimethyl-1-(2-deoxy-3,5-di-O-p-toluoyl-β-D-ribofuranosyl)-4-thiolumazine (55) in 25 mL of a saturated solution of ammonia in methanol for 16 h to 100° C. After cooling the solution was evaporated and the residue treated with $CH_2Cl_2$. The solid material was collected, washed with ether and dried in high vacuum to give 56 as 0.207 g (91% yield) of a colorless crystal powder (m.p. >300° C. decomp.).

Analysis calculated for $C_{13}H_{17}N_5O_4 \cdot H_2O$ C 49.36, H 5.74, N 22.14. Found: C 49.17, H 5.47, N 21.80.

f) 6,7-Dimethyl-4[-2-(4-nitrophenyl)ethoxycarbonyl] amino-1-(2-deoxy-β-D-ribofuranosyl)-pteridine-2-one (57)

A mixture of 1.54 g (5 mmol) of 4-amino-6,7-dimethyl-1-(2-deoxy-β-D-ribofuranosyl)-pteridine-2-one (56) and 1.87 g (6 mmol) of 1-methyl-3-[2(4-nitrophenyl)ethoxycarbonyl]imidazolium chloride (see Himmelsbach, et al. *Tetrahedron* 40: 59 (1984) which is herein incorporated by reference) in 80 mL of anhydrous DMF was stirred at room temperature over night. To this solution was slowly added 100 mL of $H_2O$ with stirring. The solution was then cooled and the precipitate collected by suction and, after washing with methanol and ether and drying in a desiccator, gave 57 as 2.0 g (80% yield) of crude material. Recrystallization from methanol yielded 1.5 g (60% yield) of colorless crystals (m.p. 154°–155° C.).

Analysis calculated for $C_{22}H_{24}N_6O_8 \cdot H_2O$: C, 50.96; H, 5.01; N, 16.21. Found: C, 50.51; H, 5.15; N, 15.84.

g) 6,7-Dimethyl-4-[2-(4-nitrophenyl)ethoxycarbonyl] amino-1-(2-deoxy-5-0-dimethoxytritylβ-D-ribofuranosyl)-pteridine-2-one (58)

Water was removed from 2.0 g (4 mmol) of 6,7-dimethyl-4-[2-(4-nitrophenyl)ethoxycarbonyl]amino-1-(2deoxy-β-D-ribofuranosyl)-pteridine-2-one (57) by twice coevaporating the crystals with 20 mL of anhydrous pyridine. The residue was dissolved in 100 mL of dry pyridine to which 1.63 g (4.8 mmol) of dimethoxytrityl chloride was added. The mixture was then stirred for 18 hours at room temperature. The reaction was quenched by the addition of 10 mL of methanol, then evaporated and finally the residue was dissolved in $CH_2Cl_2$. The solution was treated with a saturated aqueous solution of sodium bicarbonate. After separation the organic layer was dried over sodium sulfate, filtered, and evaporated again. The residue was dissolved in a little $CHCl_3$, put onto a silica-gel column and then eluted with a gradient of toluene/ethyl acetate 4:1 to 1:1. The main fraction was obtained with toluene/ethyl acetate 2:1 and gave on evaporation 58 as 2.84 g (88% yield)) of a colorless amorphous solid.

Analysis calculated for $C_{43}H_{42}N_6O_{10}$: C, 64.33; H, 5.27; N, 10.47. Found: C, 64.51; H 5.23; N, 10.24.

h) 6,7-Dimethyl-4-[2-(4-nitrophenyl)ethoxycarbonyl]amino-1-(2-deoxy-5-O-dimethoxy-trityl-β-D-ribofuranosyl)-pteridine-2-one-3'-O-(β-cyanoethyl, N-diisopropyl)phosphoramidite (59)

To 40 mL of dry $CH_2Cl_2$ and 20 mL of dry acetonitrile were added 1.0 g (1.25 mmol) of 6.7-dimethyl-4-[2-(4-nitrophenyl)ethoxycarbonyl]amino-1-(2-deoxy-5-0-dimethoxytrityl-β-D-ribofuranosyl)-pteridine-2-one (58), 44 mg (0.63 mmol) of tetrazole and 0.754 g (2.5 mmol) of β-cyanoethoxy-bis-diisopropylamino-phosphane with stirring. After 18 hours the solution was diluted with 50 mL of $CH_2Cl_2$, then extracted with a saturated aqueous solution of sodium bicarbonate, the organic layer was dried over sodium sulfate and finally evaporated. The residue was dissolved in a little $CH_2Cl_2$ and then purified by column chromatography on a silica-gel with a gradient of toluene/ethyl acetate 4:1 to 1:1. The main fraction gave on evaporation and drying in high vacuum 59 as 0.98 g (78% yield) of an amorphous solid.

Analysis calculated for $C_{52}H_{59}N_8O_{11}$ (1003.1): C, 62.27; H, 5.93; N, 11.17. Found: C, 62.00; H, 6.01; N 10.65.

EXAMPLE 9

Synthesis of a Phosphoramidite of Formula VII: 2-amino-6-methyl-4-p-nitrophenylethyl-8-(5-O-dimethoxytrityl-2-deoxy-β-D ribofuranosyl)-pteridine-7-one-3'-O-(β-cyanoethyl, N-diisopropyl)phosphoramidite (71).

The synthesis of 5,6-diamino-2-methylthio-pyrimidine-4-one (2-methylmercapto-4,5-diamino-6-oxypyrimidine), steps (a) through (c) was performed as described by Johns et al., *J. Biol. Chem.*, 14: 381–388 (1913).

a) 2-methylmercapto-4-amino-6-oxo-pyrimidine (42)

The synthesis of 2-methylmercapto-4-amino-6-oxypyrimidine was described by Johns et al., *J. Biol. Chem.*, 14: 381–387 (1913) and illustrated in Example 6, step (a).

b) 2-methylmercapto-4-amino-5-nitroso-6-oxypyrimidine (60)

To 350 mL of $H_2O$ were added 20 g of 2-methylmercapto-4-amino-6-oxypyrimidine (42) and 5.1 g NaOH. A solution of sodium nitrite in 40 mL of water was added. The mixture was then acidified by the gradual addition of 17 g of glacial acetic acid. The precipitate which formed was white, but turned blue in a short time. The mixture was allowed to remain at room temperature overnight after which the precipitate was filtered off, washed with cold water and used, without drying, for the preparation of 2-methylmercapto-4,5-diamino-6-oxypyrimidine. The yield of the nitroso derivative was almost quantitative. It was but slightly soluble in hot water or alcohol and was not soluble in benzene. It formed a red solution in alkalies and blue in acids. A portion was purified for analysis by dissolving it in ammonia and precipitating with acetic acid. The substance did not melt, but began to decompose at about 255° C.

Analysis calculated for $C_5HO_2N_4S$: N, 30.10. Found N, 30.16.

c) 5,6-diamino-2-methylthio-pyrimidine-4-one (61)

To a 1 L flask was added 50 mL of a 10 percent solution of ammonium sulphide. The solution was heated on a steam bath. The moist 2-methylmercapto-4-amino-5-nitroso-6-oxy-pyrimidine (60) obtained in the previous experiment was added gradually. Ammonium sulphide was also added when the solution turned red as this indicated that the nitroso compound was present in excess. When the ammonium sulphide was present in excess the solution was yellow. When all of the nitroso compound was reduced the addition of excess ammonium sulphide should be avoided or the diamino compound obtained will be highly colored.

d) 6-Ethoxycarbonylmethyl-2-methylthio-pteridine-4,7-dione (62)

A mixture of 17.2 g (0.1 mol) of 5,6-diamino-2-methylthio-pyrimidine-4-one (61) and 22.6 g of sodium ethyl oxalylacetate was heated in 200 mL of glacial acetic acid to 80° C. for 30 minutes. After cooling the precipitate was collected, washed with $H_2O$ and dried. The crude material was then dissolved again by heating in $EtOH/H_2O$ 1:1 and 170 mL of saturated $NaHCO_3$ solution was added. The hot solution was treated with charcoal, filtered and the filtrate poured slowly into 200 mL of hot glacial acetic acid with stirring. The yellowish precipitate was faltered off, washed with $H_2O$ and ethanol and dried at 100° C. to give 62 as 18.9 g (64%) of glittering crystals of m.p. 213° C. Analysis calculated for $C_{11}H_{12}N_4O_4S$ (296.3): C, 44.59; H, 4.08; N, 18.91 Found: C, 44.49; H, 4.03; N, 18.88.

e) 6-Methyl-2-methylthio-pteridine-4,7-dione (63)

A solution of 19.7 g (66.5 mmol) of 6-ethoxycarbonyl-methyl-2-methylthio-pteridine-4,7-dione (62) in 120 mL of 2.5 N NaOH was stirred at 80° C. for 30 min. The hot solution was treated with charcoal, filtered and the filtrate added slowly into 50 mL of hot glacial acetic acid. The precipitate was collected after cooling, washed with $H_2O$ and acetone and dried at 100° to give 63 as 14.3 g (96%) of a yellow crystalline powder (m.p.275° C. decomp.).

Analysis calculated for $C_8H_8N_4O_2S$ (224.3); C, 42.85; H, 3.60; N, 24.99. Found: C, 42.79; H, 3.59; N, 25.06.

f) 6-Methyl-2-methylthio-8-(3,5-di-O-p-toluoyl-2-deoxy-β-D-ribofuranosyl)-pteridine-4,7-dione (64)

To a suspension of 4.0 g (17.83 mmol) of 6-methyl-2-methylithio-pteridine-4,7-dione (64) in 240 mL of anhydrous acetonitrile was added 8 mL (53.6 mmol) of DBU. The mixture was stirred for 30 minutes at room temperature. To the resulting clear solution were added 4.62 g (11.9 mmol) of 3,5-di-O-p-toluoyl-2-deoxy-α-D-ribofuranosyl chloride (16) and then the mixture was stirred for 6 hours at room temperature with moisture excluded. To this solution was added 2.4 mL glacial acetic acid in 100 mL of dicholoromethane. The solution was stirred for 5 minutes and then evaporated to dryness under reduced pressure to give a syrupy residue which was chromatographed on a silica gel column (16×8.5 cm) first with 2.5 L of toluene/ethyl acetate 1:1, then 2.5 L of toluene/ethyl acetate 1:2 and finally 3 L of dichloromethane/methanol 100:3. The product fraction was collected, evaporated and the residue recrystallized from toluene to give 64 as 2.12 g (31%) of colorless crystals (m.p. 196°–197° C.).

Analysis calculated for $C_{29}H_{28}N_4O_7S$ (576.6): C, 60.41; H, 4.89; N, 9.72. Found: C, 60.26; H, 4.96; N, 9.68.

g) 6-Methyl-2-methylthio-4-p-nitrophenylethoxy-8-(3,5-di-O-p-toluoyl-2-deoxy-β-D-ribofuranosyl)-pteridine-7-one (65)

To a solution of 2.19 g (3.8 mmol) of 6-methyl-2-methylthio-8-(3,5-di-O-p-toluoyl-2-deoxy-β-D-ribofuranosyl)-pteridine-4,7-dione (64), 9.95 g (5.69 mmol)of p-nitrophenylethanol and 1.52 g (5.69 mmol) of triphenylphosphane in 75 mL of dioxan was added 1.16 g (5.7 mmol) of ethyl azodicarboxylate. The mixture stirred for 2.5 hours at room temperature. The solvent was removed under reduced pressure and the residue purified by silica gel column (5.3×15 cm) flash chromatography using 300 mL of toluene, 250 mL toluene/ethyl acetate 8:1 and 650 mL of toluene ethyl acetate 6:1. The product fraction was collected, evaporated to dryness and the residue recrystallized from $CH_2Cl_2$/AcOEt to give 65 as 2.31 g (85%) of colorless crystals (m.p. 122°–125° C.).

Analysis calculated for $C_{37}H_{35}N_5O_9S$ (727.8): C, 61.23; H, 4.86; N, 9.65. Found: C, 61.18; H, 4.95; N, 9.67.

h) 6-Methyl-2-methylsulfonyl-4-p-nitrophenylethoxy-8-(3,5-di-O-P-toluoyl-2-deoxy-β-D-ribofuranosyl)-pteridine-7-one (66)

To a solution of 2.27 g (3.13 mmol) of 6-methyl-2-methylthio-4-p-nitrophenylethoxy-8-(3,5-di-O-p-toluoyl-2-deoxy-β-D-ribofuranosyl)-pteridine-7-one (65) in 100 mL anhydrous $CH_2Cl_2$ were added with stirring 1.35 g (>6.25 mmol) of m-chloro-perbenzoic acid (80–90% purity). After stirring for 24 hours, the solution was concentrated under reduced pressure to 10 mL and the precipitate of m-chlorobenzoic acid filtered off, washed with $CH_2Cl_2$ (92×5 ml) and then both filtrates evaporated. The residue was put onto a silica gel column (5.3×14 cm) and the produce eluted by toluene/AcOEt 5:2. The product fraction was concentrated to a small volume whereby 66 crystallized out of solution producing 2.4 g (86%) of colorless crystals(m.p. 193° C.).

Analysis calculated for $C_{37}H_{35}N_5O_{11}S$ (757.8): C, 58.65; H, 4.66; N, 9.24. Found: C, 58.77; H, 4.69; N, 9.30.

i) 2-Amino-6-methyl-4-p-nitrophenylethoxy-8-(3,5-di-O-p-toluoyl-2-deoxy-β-D-ribofuranosyl)-pteridine-7-one (67)

While stirring, a solution of 1.89 g (2.5 mmol) of 6-methyl-2-methylsulfonyl4-p-nitrophenylethoxy-8-(3,5-di-O-p-toluoyl-2-deoxy-β-D-ribofuranosyl)-pteridine7-one (66) was bubbled with gaseous $NH_3$ for 80 minutes. The solution was then evaporated, twice coevaporated with $CH_2Cl_2$ and the resulting residue was put onto a silica gel column (5.5×8 cm) for chromatography with toluene/AcOEt 5:2. The product fraction was concentrated to a small volume whereby 67 crystallized out of solution as 1.68 g (97%) of colorless crystals (m.p. 208°–209° C.).

Analysis calculated for $C_{36}H_{34}N_6O_9$ (694.7): C, 62.24; H, 4.93; N, 12.10. Found: C, 61.98; H, 4.94; N, 12.14.

j) 2-Amino-6-methyl-4-p-nitrophenylethoxy-8-(2-deoxy-β-D-ribofuranosyl)-pteridine-7-one (68)

To a solution of 1.17 g (1.69 mmol) of 2-amino-6-methyl-4-p-nitrophenylethoxy-8-(3,5-di-O-p-toluoyl-2-deoxy-β-D-ribofuranosyl)-pteridine-7-one (67) in 30 mL of $CH_2Cl_2$ and 60 mL of MeOH was added 0.45 g (3.37 mmol) of sodium thiophenolate. The solution was stirred at room temperature for 16 hours. Then 11 g of flash silica gel was added to the reaction mixture and evaporated under reduced pressure. The resulting powder was put onto a silica gel column (5.3×8.5 cm) previously equilibrated with $CH_2Cl_2$/MeOH mixtures (500 ml of 100:1, 300 ml of 50:1 and 500 ml of 9:1). The product fractions were pooled and evaporated to yield 68 as 0.63 g (81%) of a microcrystalline powder (m.p. >220° C. decomp.).

Analysis calculated for $C_{20}H_{22}N_6O_7$ (458.4): C, 52.40; H, 4.84; N, 18.34. Found: C, 52.31; H, 4.76; N, 18.22.

k) 2-Amino-6-methyl-8-(2-deoxy-β-D-ribofuranosyl)-pteridine-4,7-dione[6-Methyl-8-(2-deoxy-β-D-ribofuranosyl)-isoxanthopterin (69)

To a solution of 0.195 g (0.425 mmol) of 2-amino-6-methyl-4-p-nitrophenyl-ethoxy-8-(2-deoxy-β-D-ribofuranosyl)-pteridine-7-one (68) in 15 mL of pyridine was added with 1.12 mL (1.14 mmol) of DBU. The solution was stirred for 3 hours at room temperature. The solution was then evaporated under reduced pressure, the residue dissolved in 25 mL of $H_2O$, and washed with $CH_2Cl_2$ (3×25 ml). The aqueous phase was neutralized by HCl to pH7 and then concentrated to a small volume (5 mL). The mixture was placed in the ice-box and 69 precipitated as 0.94 g (71%) of colorless crystals (m.p. >300° C. decomp.).

Analysis calculated for $C_{12}H_{15}N_5O_5 \times \frac{1}{2}H_2O$ (318.3): C, 54.28; H, 5.06; N, 22.00. Found: C, 45.42; H, 4.91; N, 21.86.

l) 2-Amino-6-methyl-4-p-nitrophenylethoxy-8-(5-O-dimethoxytrityl-2-deoxy-β-D-ribofuranosyl)-pteridine-7-one (70)

To a solution of 0.57 g (1.22 mmol) of 2-amino-6-methyl-4-p-nitrophenyl-ethoxy-8-(2-deoxy-β-D-ribofuranosyl)-pteridine-7-one (69) in 15 mL of anhydrous pyridine was added 0.454 g (1.34 mmol) of dimethoxytrityl chloride. The mixture was stirred for 1.5 hours at room temperature. Then, 5 mL of MeOH were added, the solution was stirred for 5 min and then diluted by 100 mL of $CH_2Cl_2$. The resulting solution was washed with 100 mL of saturated NaHCO3 solution and twice with $H_2O$ (100 mL). The organic layer was dried over $Na_2SO_4$, evaporated and the residue put onto a silica gel column (3×15 cm) for chromatography with toluene/AcOEt 1:1. The product fraction was evaporated to give 70 as 0.5 g (54%) of a solid foam.

Analysis calculated for $C_{41}H_{40}N_6O_9$ (760.8): C, 63.14; H, 5.30; N, 11.05. Found: C, 63.06; H, 5.21; N, 10.91.

m) 2-Amino-6-methyl-4-p-nitrophenylethoxy-8-(5-O-dimethoxytrityl-2-deoxy-β-D-ribofuranosyl)-pteridine-7-one-3'-O-(β-cyanoethyl, N-diisopropyl)phosphoramidite (71)

To a solution of 0.76 g (1 mmol) of 2-amino-6-methyl-4-p-nitrophenylethoxy-8-(5-O-dimethoxytrityl-2-deoxy-β-D-ribofuranosyl)-pteridine-7-one (70) in 15 mL of anhydrous $CH_2Cl_2$, under argon atmosphere, was added 0.452 g (1.5 mmol) of 2-cyanoethoxy-bis-N,N-diisopropylaminophosphane and 35 mg (0.5 mmol) of tetrazole. The solution was stirred for 12 hours at room temperature. The mixture was then diluted with 15 mL of $CH_2Cl_2$ and extracted once with 10 mL of a saturated $NaHCO_3$ solution and twice with a saturated NaCl solution. The organic layer was dried over $Na_2SO_4$, evaporated and the residue put onto a silica gel column for chromatography with toluene/AcOEt 3:2 containing a small amount of triethylamine. The product fraction was collected, evaporated to a yellowish foam which was dissolved in little toluene and added dropwise into 100 mL of n-hexane with stirring to give, after filtration by suction and drying, 71 as 0.865 g (90%) of a yellowish powder (m.p. >150° C. decomp.).

Analysis calculated for $C_{50}H_{57}N_8O_{10}P$ (960.9): C, 62.97; H, 5.98; N, 12.32. Found: C, 62.81; H, 5.88; N, 12.20.

EXAMPLE 10

General Synthesis of 2'-deoxy-β-D-ribofuranosyl-pteridine-5'-triphosphates a) triethylammonium pteridine-2'-deoxyribonucleoside-5'-monophosphate (72)

To 15 mL of trimethyl phosphate is added 6.5 mmoles of the appropriate pteridine-β-D-2'-deoxyribonucleoside. The mixture is cooled to −6° C. excluding all moisture. The mixture was then stirred and 1.5 mL (16.3 mmole) of $POCl_3$ was added dropwise over a period of 5 minutes, after which the mixture is stirred for 2 h at 0° C. to obtain a clear solution. To the solution is added 120 mL of 0.5M triethylammonium bicarbonate buffer pH 7.5. The solution is stirred for 15 minutes and then evaporated in vacuo. After several coevaporations with methanol, the residue is dissolved in $H_2O$ and put onto a DEAE-Sephadex column (2.5×80 cm; $HCO_3$-form). Chromatography is performed using a linear gradient of 0–0.3M triethylammonium bicarbonate buffer pH 7.5 using 8–10 Liters of buffer.

The main fraction is eluted at a 0.2–0.3M buffer concentration. This fraction is evaporated in vacuo at 30° and then the resulting residue coevaporated several times with methanol. Drying in high vacuum gives solid 72.

b) triethylammonium pteridine-2'-deoxyribonucleoside-5'-triphosphate (73)

The triethylammonium pteridine-2'-deoxyribonucleoside-5'-monophosphate (58) (1 mmole) is coevaporated three times with anhydrous pyridine and then dissolved in 10 mL of anhydrous dimethylformamide (DMF). The solution is stirred overnight after addition of 0.8 g (5 mmole) of carbonyldimidazole under anhydrous conditions. Excess carbonyldimidazole is quenched by the adding of 0.33 mL of anhydrous methanol to the solution and stirring for 1 hour. To this solution is added a suspension of 5 mmole of tributylammonium pyrophosphate in 50 mL of anhydrous DMF. The mixture is then stirred continuously for 20 hours at room temperature. The resulting precipitate is filtered off, washed with DMF and the filtrate evaporated under high vacuum at 30° C. The residue is coevaporated several times with methanol and $H_2O$, then dissolved in $H_2O$ and put onto a DEAE-Sephadex column (2.5×80 cm, $HCO_3$ form) and eluted with a linear gradient of triethylammonium bicarbonate buffer pH 7.5 using about 10 L. The product is eluted in the fractions at a buffer concentration of 0.7M. The fractions are pooled, evaporated, and then coevaporated several times with methanol. The mixture is then dried under high vacuum to give an 73 as an amorphous solid.

c) sodium pteridine-2'-deoxyribonucleoside-5'-triphosphate (74)

In 10 mL of anhydrous methanol is dissolved 0.5 mmole of triethylammonium Pteridine-2'-deoxyribonucleoside-5'-triphosphate (73). The solution is stirred and 1.5 equivalents of a 1N NaI solution in acetone is slowly added dropwise producing a precipitate of the sodium salt. The suspension is diluted with 100 mL of acetone, stirred for 30 minutes and then the solid is collected by suction through a porcelain funnel. The solid is washed with small portions of acetone and dried under high vacuum to give the 74 which is more stable then the trierthyklammonium salt and can be stored without decomposition.

EXAMPLE 11

Synthesis of Oligonucleotides Containing Pteridine Derivatives

The following oligonucleotides were synthesized on an ABI DNA synthesizer (model 380B, Applied Biosystems, Foster City, Calif.):

| | |
|---|---|
| Oligo 1: | 5'- GTψ TGG AAA ATC TCT AGC AGT -3', |
| Oligo 2: | 5'- GTG TψG AAA ATC TCT AGC AGT -3', |
| Oligo 3: | 5'- GTG TGψ AAA ATC TCT AGC AGT -3', |
| Oligo 4: | 5'- GTG TGG AAA ATC TCT AOC AGT -3', |
| Oligo 5: | 5'- GTG TGG AAA ATC TCT AGC AψT -3', |
| Oligo 6: | 5'- GTG TcG AAA ATC TCT AψC AGT -3', |
| Oligo 7: | 5'- ACT GCT AGA ψAT TTT CCA CAC -3', |
| Oligo 8: | 5'- ACT GCT AψA GAT TTT CCA CAC -3', |
| Oligo 9: | 5'- ACT ψCT AGA GAT TTT CCA CAC -3' and |
| Oligo 10: | 5'- ACT GCT ψGA GAT TTT CCA CAC -3'. |

In each oligonucleotide one or more guanosines was replaced by the pteridine deoxyribonucleotide (designated ψ) of formula XVI.

To synthesize the oligonucleotides containing the pteridine nucleotide, the dimethoxytrityl blocked pteridine phosphoramidite was placed in bottle port #5 on the DNA synthesizer. No changes in synthesis protocol were necessary to achieve incorporation of the pteridine nucleotide.

The oligonucleotides were cleaved from the solid support by treatment with concentrated ammonia, and deprotected by heating the ammonia solution to 55° C. for 8 hours. Samples where then evaporated to dryness in a Speed Vac Concentrator (Savant, Farmingdale, N.Y., USA). The oligonucleotides were purified by 19:1 20% polyacrylamide gel electrophoresis. Bands were detected by UV shadowing, excised, and eluted into 0.3M sodium acetate pH 5.2 using a crush and soak method. Finally, after addition of $MgCl_2$ to achieve a concentration of 0.1M, samples were precipitated in ethanol.

Fluorescent analysis of the oligonucleotides in TRIS buffer at pH 7.8 revealed the relative quantum yields shown below in Table 1. Fluorescence measurements were made using an excitatory wavelength of 360 nm. Quinine sulfate was used as the standard and measurements were taken on a fluorometer (model 8000, SLM-Aminco, Urbana, Ill., U.S.A.).

TABLE 1

Relative quantum yields of oligonucleotides containing pteridine nucleotides substituted for guanosine at various positions.

| Oligonucleotide | Relative Quantum Efficiency |
|---|---|
| 5'- GTψ TGG AAA ATC TCT AGC AGT -3' | 0.12–0.17 |
| 5'- GTG TψG AAA ATC TCT AGC AGT -3' | 0.09–0.15 |
| 5'- GTG TGψ AAA ATC TCT AGC AGT -3' | 0.02–0.03 |
| 5'- GTG TGG AAA ATC TCT AψC AGT -3' | 0.04–0.07 |
| 5'- GTG TGG AAA ATC TCT AGC AψT -3' | 0.14 |
| 5'- GTG TOG AAA ATC TCT AψC AGT -3' | 0.10 |
| 5'- ACT GCT AGA ψAT TTT CCA CAC -3' | 0.03–0.04 |
| 5'- ACT GCT AψA GAT TTT CCA CAC -3' | 0.02–0.03 |
| 5'- ACT ψCT AGA GAT TTT CCA CAC -3' | 0.24–0.39 |
| 5'- ACT GCT ψGA GAT TTT CCA CAC -3' | 0.23 |

EXAMPLE 12

Realtime Detection of Integrase Activity Utilizing Oligonucleotides Containing Pteridine Derivatives.

The oligonucleotide 5'-GTGTGGAAAATCTCTAGCAψT -3' and its complement 5'- ACTGCTAGAGATTTTCCACAC -3' were synthesized according to the method of Example 11. The oligonucleotides were then annealed together by heating them to 85° C. in a 100 mM NaCl solution and allowing the solution to slowly cool to room temperature. This formed the model substrate, a double-stranded DNA molecule:

5'-GTG TGG AAA ATC TCT AGC AψT -3'

3'- CAC ACC TTT TAG AGA TCG TCA -5' where ψ represents the pteridine nucleotide.

HIV-1 integrase protein (3.5 pmol per reaction) was produced via an *Echerichia coli* expression vector, as described by Bushman et al. *Science*, 249: 1555–1558 (1990). The protein was stored at −70° C. in 1M NaCl/20 mM Hepes, pH 7.6/1 mM EDTA/1 mM dithiothreitol/20% glycerol (wt/vol).

The stock protein (0.44 mg/ml) was first diluted 1:3 in protein storage buffer (1M NaCl/20 mM Hepes, pH 7.6/1 mM EDTA/1 mM dithiothreitol/20% (wt/vol) glycerol). Subsequent enzyme dilution was at 1:20 in reaction buffer (25 mM Mops, pH 7.2/7.5 mM $MnCl_2$/bovine serum albumin at 100 µg/ml/10 mM 2-mercaptoethanol). The reaction volume is 60 µl. The final reaction mixture contained 50 mM NaCl, 1 mM Hepes, 50 µM EDTA and 50 µM dithiothreitol, 10% (wt/vol) glycerol, 7.5 mM $MnCl_2$, 0.1 mg/ml bovine serum albumin, 10 mM 2-mercaptoethanol, and 25 mM MOPS, pH 7:2.

The reaction was initiated by addition of the enzyme and was monitored for 10 to 20 minutes in real time by observing the change in fluorescence intensity using a fluorometer (model 8000, SLM-Aminco, Urbana, Ill., U.S.A.). The excitation wavelength was 360 nm and the emission wavelength was 460 nm.

The integrase reacted with the model substrate shown above to produce:

5'-GTG TGG AAA ATC TCT AGC A -3'+ψT
3'-CAC ACC TTT TAG AGA TCG TCA -5'

The fluorescence of the pteridine nucleotide was quenched considerably when it was incorporated into the oligonucleotide (quantum yield of 0.14). The cleavage reaction released this quench resulting in a four-fold increase in the signal (quantum yield of 0.88 for the monomer). Thus the activity of integrase was assayed by measuring the increase in fluorescence.

What is claimed is:

1. An oligonucleotide comprising one or more nucleotide monomers which are pteridine derivatives having the formula shown below, with ring vertices 1 through 8 as shown:

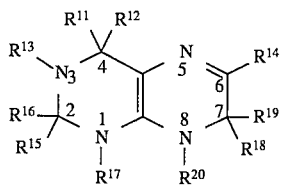

in which:

ring vertices 2 and 4 collectively bear at most one oxo oxygen $R^{11}$ is combined with $R^{12}$ to form a single oxo oxygen joined by a double bond to ring vertex 4, or with $R^{13}$ to form a double bond between ring vertices 3 and 4;

$R^{12}$ when not combined with $R^{11}$ is $NH_2$;

$R^{13}$ when not combined with $R^{11}$ is lower alkyl or H;

$R^{14}$ is a member selected from the group consisting of H, lower alkyl and phenyl;

$R^{15}$ is combined with $R^{16}$ to form a single oxo oxygen joined by a double bond to ring vertex 2, or with $R^{17}$ to form a double bond between ring vertices 1 and 2, $R^{16}$ when not combined with $R^{15}$ is a member selected from the group consisting of H, phenyl, and $NH_2$;

when $R^{15}$ is not combined with $R^{16}$, $R^{18}$ is combined with $R^{19}$ to form a single oxo oxygen joined by a double bond to ring vertex 7;

when $R^{15}$ is combined with $R^{16}$, $R^{18}$ is combined with $R^{20}$ to form a double bond between ring vertices 7 and 8, and $R^{19}$ is a member selected from the group consisting of H and lower alkyl; and $R^{17}$ when not combined with $R^{15}$, or $R^{20}$ when not combined with $R^{18}$, is

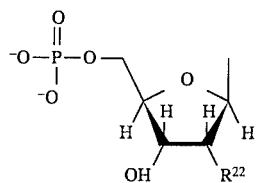

in which $R^{22}$ is a member selected from the group consisting of H and OH.

2. A compound in accordance with claim 1 in which $R^{14}$ is a member selected from the group consisting of H, $CH_3$ and phenyl.

3. A compound in accordance with claim 1 in which $R^{14}$ is a member selected from the group consisting of H and $CH_3$.

4. A compound in accordance with claim 1 in which $R^{16}$, when not combined with $R^{15}$, is a member selected from the group consisting of H, phenyl and $NH_2$.

5. A compound in accordance with claim 1 in which $R^{16}$, when not combined with $R^{15}$, is a member selected from the group consisting of H and phenyl.

6. A compound in accordance with claim 1 in which, when $R^{18}$ is combined with $R^{20}$, $R^{19}$ is a member selected from the group consisting of H and $CH_3$.

7. A compound in accordance with claim 1 in which $R^{14}$ is a member selected from the group consisting of H, $CH_3$ and phenyl; $R^{16}$ is a member selected from the group consisting of H, phenyl and $NH_2$; and, when $R^{18}$ is combined with $R^{20}$, $R^{19}$ is a member selected from the group consisting of H and $CH_3$.

8. A compound in accordance with claim 1 in which:

$R^{11}$ is combined with $R^{13}$ to form a double bond between ring vertices 3 and 4;

$R^{12}$ is $NH_2$;

$R^{14}$ is H;

$R^{15}$ is combined with $R^{17}$ to form a double bond between ring vertices 1 and 2;

$R^{16}$ is phenyl;

$R^{18}$ is combined with $R^{19}$ to form a single oxo oxygen joined by a double bond to ring vertex 7; and $R^{20}$ is

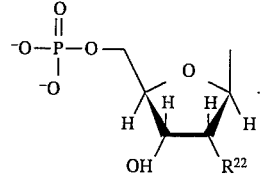

9. A compound in accordance with claim 1 in which:

$R^{11}$ is combined with $R^{13}$ to form a double bond between ring vertices 3 and 4;

$R^{12}$ is $NH_2$;

$R^{14}$ is phenyl;

$R^{15}$ is combined with $R^{17}$ to form a double bond between ring vertices 1 and 2;

$R^{16}$ is H;

$R^{18}$ is combined with $R^{19}$ to form a single oxo oxygen joined by a double bond to ring vertex 7; and $R^{20}$ is

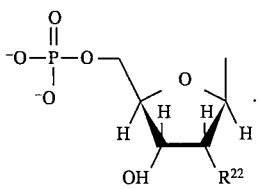

10. A compound in accordance with claim 1 in which:

$R^{11}$ is combined with $R^{12}$ to form a single oxo oxygen joined by a double bond to ring vertex 4;

$R^{13}$ is $CH_3$;

$R^{14}$ is H;

$R^{15}$ is combined with $R^{17}$ to form a double bond between ring vertices 1 and 2;

$R^{16}$ is $NH_2$;

$R^{18}$ is combined with $R^{19}$ to form a single oxo oxygen joined by a double bond to ring vertex 7; and $R^{20}$ is

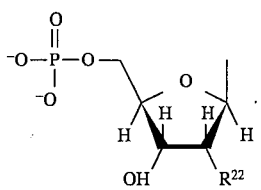

11. A compound in accordance with claim 1 in which:

$R^{11}$ is combined with $R^{12}$ to form a single oxo oxygen joined by a double bond to ring vertex 4;

$R^{13}$ is H;

$R^{14}$ is H;

$R^{15}$ is combined with $R^{17}$ to form a double bond between ring vertices 1 and 2;

$R^{16}$ is $NH_2$;

$R^{18}$ is combined with $R^{19}$ to form a single oxo oxygen joined by a double bond to ring vertex 7; and $R^{20}$ is

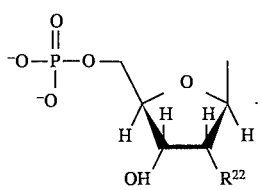

12. A compound in accordance with claim 1 in which:

$R^{11}$ is combined with $R^{12}$ to form a single oxo oxygen joined by a double bond to ring vertex 4;

$R^{13}$ is H;

$R^{14}$ is $CH_3$;

$R^{15}$ is combined with $R^{17}$ to form a double bond between ring vertices 1 and 2;

$R^{16}$ is $NH_2$;

$R^{18}$ is combined with $R^{19}$ to form a single oxo oxygen joined by a double bond to ring vertex 7; and $R^{20}$ is

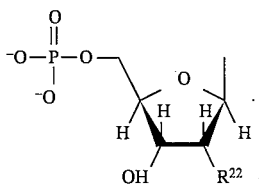

13. A compound in accordance with claim 1 in which:

$R^{11}$ is combined with $R^{13}$ to form a double bond between ring vertices 3 and 4;

$R^{12}$ is $NH_2$;

$R^{14}$ is $CH_3$;

$R^{15}$ is combined with $R^{16}$ to form a single oxo oxygen joined by a double bond to ring vertex 2;

$R^{17}$ is

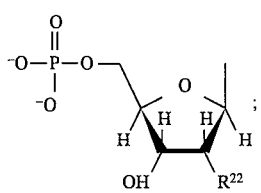

$R^{18}$ is combined with $R^{20}$ to form a double bond between ring vertices 7 and 8; and $R^{19}$ is $CH_3$.

14. A compound in accordance with claim 1 in which:

$R^{11}$ is combined with $R^{13}$ to form a double bond between ring vertices 3 and 4;

$R^{12}$ is $NH_2$;

$R^{14}$ is H;

$R^{15}$ is combined with $R^{16}$ to form a single oxo oxygen joined by a double bond to ring vertex 2;

$R^{17}$ is

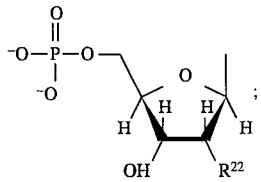

$R^{18}$ is combined with $R^{20}$ to form a double bond between ring vertices 7 and 8; and $R^{19}$ is $CH_3$.

15. A compound in accordance with claim 1 in which:

$R^{11}$ is combined with $R^{13}$ to form a double bond between ring vertices 3 and 4;

$R^{12}$ is $NH_2$;

$R^{14}$ is $CH_3$;

$R^{15}$ is combined with $R^{16}$ to form a single oxo oxygen joined by a double bond to ring vertex 2;

$R^{17}$ is

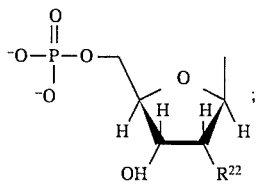

$R^{18}$ is combined with $R^{20}$ to form a double bond between ring vertices 7 and 8; and $R^{19}$ is H.

16. A compound in accordance with claim 1 in which:

$R^{11}$ is combined with $R^{13}$ to form a double bond between ring vertices 3 and 4;

$R^{12}$ is $NH_2$;

$R^{14}$ is H;

$R^{15}$ is combined with $R^{16}$ to form a single oxo oxygen joined by a double bond to ring vertex 2;

$R^{17}$ is

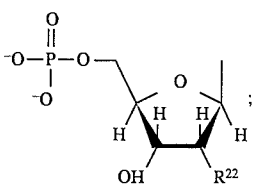

$R^{18}$ is combined with $R^{20}$ to form a double bond between ring vertices 7 and 8; and $R^{19}$ is H.

17. A compound in accordance with claim 1 in which said nucleotide monomers are at the 3' end of said oligonucleotide.

18. A compound in accordance with claim 1 in which said nucleotide monomers are at the 5' end of said oligonucleotide.

19. A compound in accordance with claim 1 in which said nucleotide monomers are surrounded by 1 to 10 pyrimidine monomers.

20. A compound in accordance with claim 1 selected from the group consisting of:

5'-GTψ TGG AAA ATC TCT AGC AGT-3',

5'-GTG TψG AAA ATC TCT AGC AGT-3',

5'-GTG TGψ AAA ATC TCT AGC ACT-3',

5'-GTG TGG AAA ATC TCT AψC ACT -3',

5'-GTG TGG AAA ATC TCT AGC AψT-3',

5'-GTG TψG AAA ATC TCT AψC ACT-3',

5'-ACT GCT AGA ψAT TTT CCA CAC-3',

5'-ACT GCT AψA GAT TTT CCA CAC-3',

5'-ACT ψCT AGA GAT TTT CCA CAC-3' and

5'-ACT GCT ψGA GAT TTT CCA CAC-3', wherein A is an adenosine nucleotide, C is a cytosine nucleotide, G is a guanosine nucleotide, T is a thymidine nucleotide, and ψ is a pteridine nucleotide in which $R^{11}$ is combined with $R^{12}$ to form a single oxo oxygen joined by a double bond to ring vertex 4; $R^{13}$ is $CH_3$ or H; $R^{14}$ is H; $R^{15}$ is combined with $R^{17}$ to form a double bond between ring vertices 1 and 2; $R^{16}$ is $NH_2$; $R^{18}$ is combined with $R^{19}$ to form a single oxo oxygen joined by a double bond to ring vertex 7; and $R^{20}$ is

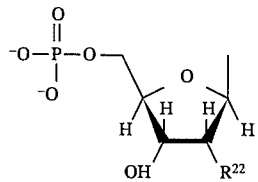

in which $R^{22}$ is H.

* * * * *

UNITED STATES PATENT AND TRADEMARK OFFICE
CERTIFICATE OF CORRECTION

PATENT NO. : 5,612,468  
DATED : March 18, 1997  
INVENTOR(S) : Hawkins et al.

Page 1 of 1

It is certified that error appears in the above-identified patent and that said Letters Patent is hereby corrected as shown below:

Title,
In the left-hand column of the title page, at [54], delete "Nucletide" and insert therefor -- Nucleotide --.

Column 1,
Line 1, delete "Nucletide" and insert therefor -- Nucleotide --.

Claim 20, Column 52,
Line 9, before "-3'," delete ACT and insert therefor -- AGT --.
Line 10, before "-3'," delete ACT and insert therefor -- AGT --.
Line 12, before "-3'," delete ACT and insert therefor -- AGT --.

Signed and Sealed this

Twenty-first Day of August, 2001

Attest:

NICHOLAS P. GODICI
Attesting Officer    Acting Director of the United States Patent and Trademark Office